US006853447B2

(12) United States Patent
Goetz

(10) Patent No.: US 6,853,447 B2
(45) Date of Patent: Feb. 8, 2005

(54) SYSTEM AND METHOD FOR THE COLLECTION OF SPECTRAL IMAGE DATA

(75) Inventor: Alexander Goetz, Boulder, CO (US)

(73) Assignee: Analytical Spectral Devices, Inc., Boulder, CO (US)

( * ) Notice: Subject to any disclaimer, the term of this patent is extended or adjusted under 35 U.S.C. 154(b) by 0 days.

(21) Appl. No.: 10/023,396

(22) Filed: Dec. 20, 2001

(65) Prior Publication Data

US 2002/0109835 A1 Aug. 15, 2002

Related U.S. Application Data

(60) Provisional application No. 60/268,483, filed on Feb. 12, 2001.

(51) Int. Cl.[7] .............................................. G01N 21/00
(52) U.S. Cl. ..................................... 356/237.1; 382/254
(58) Field of Search .......................... 356/237.1–237.3, 356/388, 390–394; 250/223 R, 226, 339.08, 339.12; 382/254, 260, 274, 110; 209/589; 378/57

(56) References Cited

U.S. PATENT DOCUMENTS

| | | | |
|---|---|---|---|
| 4,143,770 A | | 3/1979 | Grimmell et al. |
| 4,446,481 A | * | 5/1984 | Edamatsu et al. .......... 348/132 |
| 4,893,253 A | | 1/1990 | Lodder |
| 4,953,745 A | | 9/1990 | Rowlett, Jr. |
| 5,085,325 A | * | 2/1992 | Jones et al. ................. 209/580 |
| 5,401,059 A | | 3/1995 | Ferrario |
| 5,448,110 A | | 9/1995 | Tuttle et al. |
| 5,504,332 A | | 4/1996 | Richmond et al. |
| 5,522,512 A | | 6/1996 | Archer et al. |
| 5,558,231 A | | 9/1996 | Weier |
| 5,615,009 A | | 3/1997 | Sakura et al. |
| 5,628,530 A | | 5/1997 | Thornton |
| 5,646,425 A | | 7/1997 | Beach |
| 5,679,954 A | | 10/1997 | Soloman |
| 5,750,996 A | | 5/1998 | Drennen, III et al. |
| 5,760,399 A | | 6/1998 | Trygstad |
| 5,900,634 A | | 5/1999 | Soloman |
| 5,991,456 A | * | 11/1999 | Rahman et al. ............. 382/254 |
| 6,324,253 B1 | * | 11/2001 | Yuyama et al. ............... 378/57 |
| 6,410,872 B2 | * | 6/2002 | Campbell et al. ........... 209/577 |
| 6,587,575 B1 | * | 7/2003 | Windham et al. ........... 382/110 |

FOREIGN PATENT DOCUMENTS

| | | |
|---|---|---|
| EP | 0727671 B1 | 8/1996 |
| EP | 0841548 A2 | 5/1998 |

(List continued on next page.)

OTHER PUBLICATIONS

Proceedings of the SPIE—The International Society for Optical Engineering, vol. 2979, 1997, pp. 107–110, "Discrimination Between Scattering and Absorption Inhomogeneities Using Time–Resolved Transmittance Imaging," P. Taroni, et al.

(List continued on next page.)

Primary Examiner—Gregory J. Toatley, Jr.
Assistant Examiner—Sang H. Nguyen
(74) Attorney, Agent, or Firm—Cooley Godward LLP

(57) ABSTRACT

A method of verifying the contents of a package comprising obtaining a spectral image of a first package, the first package having a plurality of receptacles configured to receive an item, wherein the plurality of first package receptacles do not contain any items, acquiring a spectral image of a second package, the second package having a plurality of receptacles configured to receive an item, wherein the plurality of second package receptacles each contain an item, and comparing the spectral image of the first package with the spectral image of the second package wherein acquiring a spectral image of a second package comprises acquiring a plurality of spectral image lines and wherein each of the spectral image lines comprises a plurality of image pixels.

14 Claims, 18 Drawing Sheets

FOREIGN PATENT DOCUMENTS

| | | |
|---|---|---|
| EP | 0 887 638 A1 | 12/1998 |
| EP | 0 959 342 A2 | 11/1999 |
| EP | 0 959 342 A3 | 1/2000 |
| EP | 0996293 A2 * | 4/2000 |
| JP | 10363008 * | 7/2000 |
| WO | WO 96/32631 A1 | 10/1996 |
| WO | WO 97/07473 A1 | 2/1997 |
| WO | WO 98/28676 A2 | 7/1998 |
| WO | WO 00/00811 A2 | 1/2000 |
| WO | WO 00/04480 A1 | 1/2000 |
| WO | WO 01/03646 A2 | 1/2001 |
| WO | WO 01/03646 A3 | 1/2001 |
| WO | WO 01/22063 A1 | 3/2001 |
| WO | WO 02/07066 A1 | 1/2002 |

OTHER PUBLICATIONS

Journal of the Optical Society of America A, vol. 14, No. 1/Jan. 1997, pp. 235–240, "Photon Migration at Short Times and Distances and in Case of Strong Absorption," D.J. Durian, et al.

Copy of International Search Report for PCT Application Serial No. PCT/US03/07365, mailed on Jul. 27, 2004.

MacDonald B. F., et al.: "Some Applications of Near–Infrared Reflectance Analysis in the harmaceutical Industry;" Journal of Pharmaceutical and Biomedical Analysis; vol. 11, No. 11–12, 1993, pp. 1077–1085, XP001098341; ISSN: 0731–7085; p. 1079, col. 1, Paragraph 3; p. 1080, col. 2, Paragraph 3.

Aldridge P. K., et al.: "Identification of Tablet Formulations Inside Blister Packages by Near–Infrared Spectroscopy;" Applied Spectroscopy; vol. 48, No. 10, 1994, pp. 1272–1276; XP001098336; Whole Document.

Blanco, M., et al.: "Identification and Quantitation Assays for Intact Tablets of Two Related Pharmaceutical Preparations by Reflectance Near–Infrared Spectroscopy: Validation of the Procedure;" Journal of Pharmaceutical and Biomedical Analysis; vol. 22, No. 1, Feb. 2000, pp. 139–148, XP002212018; ISSN: 0731–7085; Whole Document.

Copy of the International Search Report for PCT Application Serial No. PCT/US02/03286, mailed on Oct. 14, 2002.

Copy of the International Search Report for PCT Application Serial No. PCT/US02/03287, mailed on Sep. 24, 2002.

Copy of the International Search Report for PCT Application Serial No. PCT/US02/03285, mailed on Sep. 24, 2002.

Copy of the International Search Report for PCT Application Serial No. PCT/US02/03288, mailed on Sep. 24, 2002.

* cited by examiner

SYSTEM AND METHOD FOR THE COLLECTION OF SPECTRAL IMAGE DATA

RELATED APPLICATIONS

The present application claims priority to U.S. provisional application No. 60/268,483 and titled NIR Screening of Materials To Be Packaged, filed on Feb. 12, 2001, which is hereby incorporated by reference.

The present application is based on disclosure document No. 481228 deposited with the U.S. Patent and Trademark Office on Oct. 17, 2000. The present application is also related to U.S. patent application Ser. No. 10/023,302, filed on even date herewith and titled System and Method for Combining Reflectance Data, and U.S. patent application Ser. No. 10/023,395, filed on even date herewith and titled System and Method for Grouping Reflectance Data. Each of the above documents are hereby incorporated by reference.

FIELD OF THE INVENTION

The present invention pertains to spectrometer and reflectance data analysis and more particularly to the screening and identification of materials such as pharmaceutical or food products being packaged in an automated machine.

BACKGROUND OF THE INVENTION

Optical spectrometers allow the study of a large variety of samples over a wide range of wavelengths. Materials can be studied in the solid, liquid, or gas phase either in a pure form or in mixtures. Various designs allow the study of spectra as a function of temperature, pressure, and external magnetic fields.

Near-Infrared (NIR) spectroscopy is one of the most rapidly growing methodologies in product analysis and quality control. In particular, NIR is being increasingly used as an inspection method during the packaging process of pharmaceuticals or food products. More and more often, this technique is augmenting or even replacing previously used vision inspection systems. For example, an NIR inspection system can be used to inspect a pharmaceutical blister package (such as an oral contraceptive or allergy medication) for, among other things, physical aberrations, chemical composition, moisture content, and proper package arrangement.

Most notably, NIR spectrometry inspection systems can be used to evaluate the chemical composition of products during the packaging process. Particularly with solid dosage pharmaceutical products, a group or package of products may look identical in the visible portion of the spectrum but may have unique chemical signatures in the near-infrared range (e.g. the 800–2500 nm range). Variations in the chemical composition of a tablet or capsule are usually grounds for rejecting a package containing a tablet with such a discrepancy. In operation on a pharmaceutical blister packaging machine, a still uncovered blister pack containing tablets or capsules passes an inspection station where it is examined. Once the inspection device inspects the blister pack to ensure that the correct material is located in each of the tablet or capsule wells, the packaging machine seals the blister pack. Those packages that fail the inspection process are rejected at a subsequent station. Subject to regulatory requirements, the rejected tablets may also be recycled for further processing.

The use of vision systems as an inspection mechanism continues to become less desirable as the need for more in depth inspection procedures and near 100% inspection processes are desired. Of particular concern is that known vision systems are inherently incapable of performing a chemical analysis of the product being packaged. Rather, vision systems rely solely on a comparison of a visual snapshot of the package to a previously stored reference image. Known vision packaging inspection systems "look" at each individual package to see whether it has the correct number of doses in the pack. For example, vision systems look for missing or overfilled tablet wells. In some cases, physical discrepancies, cracks, or gouges on a tablet will also cause a vision system to reject the package. What may not be detected by a vision system is the situation where each of the products in a package appears to be similar and in conformance with a reference image but the formulation of one or more products within the package are incorrect, or the wrong product composition is inserted into the packaging. The limitations of these types of known visions systems become readily apparent when higher levels of inspection are required and when they are compared with the expanded capabilities of a spectrometer-based inspection system.

Even though spectrometer-based monitoring and inspection systems are becoming more prevalent, many of them still have limited capabilities. These limitations are primarily due to the requirement that each tablet or capsule in a package be independently inspected by the spectrometer system. Therefore, a conventional spectrometer can only look at and analyze one sample at a time. Thus, the larger the number of products that are being inspected, the longer it will take to perform the inspection. Adding additional spectrometers is not a preferred solution because of the costs and maintenance issues associated with the increased hardware. Since spectrometer-based systems are meant in large part to replace vision systems, both accuracy and speed remain important factors when utilizing such systems. Thus, it would be desirable to have a spectrometer-based inspection system that can maintain the throughput of traditional vision systems without sacrificing the ability to perform accurate chemical composition analysis and without requiring the addition of expensive and problem prone equipment.

In many cases, multiple formulations are packaged into a single blister pack. Therefore, it is also desirable to have a spectrometer-based inspection system that can detect when an item is in the wrong location within the larger package that is being inspected while at the same time realizing the benefits of a spectrometer based inspection system.

Finally, it is desirable to have a spectrometer-based inspection system that can execute a self-referencing calibration in order to obtain conforming data to compare with during an inspection process as well as to determine item locations from a previously unknown package layout.

SUMMARY OF THE INVENTION

In one aspect, a method of verifying the contents of a package comprises obtaining a spectral image of a first package, the first package having a plurality of receptacles configured to receive an item, wherein the plurality of first package receptacles do not contain any items, acquiring a spectral image of a second package, the second package having a plurality of receptacles configured to receive an item, wherein the plurality of second package receptacles each contain an item, and comparing the spectral image of the first package with the spectral image of the second package wherein acquiring a spectral image of a second package comprises acquiring a plurality of spectral image lines and wherein each of the spectral image lines comprises a plurality of image pixels.

In another aspect, a method of verifying the location of package contents comprises acquiring a reflectance signal of a package, the package having a plurality of receptacles configured to receive an item, wherein each of the plurality of receptacles contains an item, wherein the reflectance signal comprises a plurality of image pixels, isolating the image pixels that correspond to each of the plurality of items, and comparing the reflectance signal of the isolated image pixels with a reference reflectance signal.

In a further aspect, a push-broom scanning spectrometer, comprises an imager adapted to simultaneously acquire a line of image pixels from a moving package, wherein the image pixel line comprises a plurality of contiguous spectral bands, wherein the image pixel line is oriented perpendicular to the direction of motion of the package, wherein the package includes a plurality of items, a conveyer system adapted to move the package through a field of view corresponding to the imager, and a processor capable of being programmed to compare the line of image pixels with a references signal and to determine the location of the plurality of items within the package based on the comparison of the line of image pixels to the reference signal.

As will become apparent to those skilled in the art, numerous other embodiments and aspects will become evident hereinafter from the following descriptions and claims.

BRIEF DESCRIPTION OF THE DRAWINGS

The drawings illustrate both the design and utility of the preferred embodiments of the present invention, wherein.

DETAILED DESCRIPTION

Figure 1:
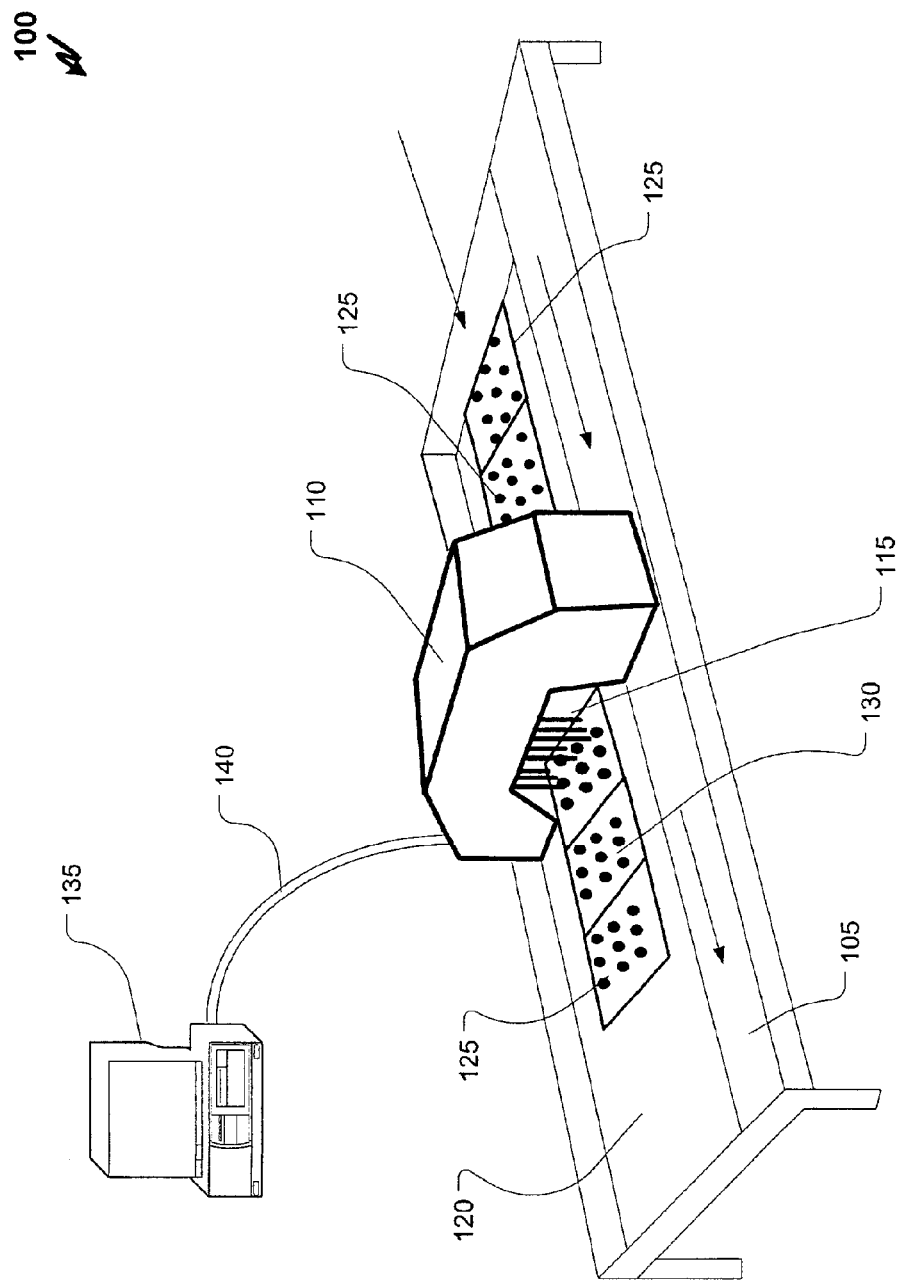
FIG. 1 is a general overview of an inspection system.

FIG. 1 depicts an inspection system 100. The inspection system 100 is generally arranged to allow the inspection of a product, for example tablets or capsules 130, that have been loaded into a package 125. As shown in FIG. 1, the packages 125 move along a conveyer 120 mounted within a filling unit 105. The filling unit 105 is preferably one component of a larger manufacturing and packaging system. As an example, such manufacturing and packaging systems are typically utilized in pharmaceutical and chemical manufacturing facilities, although similar systems are often utilized in other applications such as food processing and consumer product facilities. Aspects of the present invention can be applied to virtually any of these applications. For purposes of illustration only, the present invention will be described in conjunction with a pharmaceutical packaging system used to seal tablets or capsules in a blister-type package. Also shown in FIG. 1, and included as a component of the inspection system 100, is an inspection head 110 constructed in accordance with various aspects of the present invention.

The inspection head 110 bridges the conveyer 120 that carries the packages 125. The inspection head 1 10 includes an array of sample probes 115 extending downward from the inspection head 110 and substantially aligning with the items 130 contained in the passing packages 125. Generally, a light source (not shown) illuminates the packages 125 including the tablets 130 as they pass under the inspection head 110 and the sample probes 115. Light is reflected by the tablets 130 and the reflected light energy is gathered by one or more of the probes 115. In the general arrangement of FIG. 1, a single sample probe 115 corresponds to a single tablet. Either the web of packages 125 moves in steps, where the step increment matches the size of the packages in the direction of motion, or the web moves continuously. In the stepped progression, item inspection occurs when the package web is stationary. In the continuous progression, item inspection occurs during the time interval when the items are in the field of view of the probes 115. As discussed below, various other arrangements of the sample probes are contemplated by an inspection system constructed in accordance with the present invention.

The reflected light energy gathered by each of the probes 115 is analyzed to determine specific properties of each of the tablets 130 that pass beneath the inspection head 110. Light energy gathered by the sample probes 115 is then directed through fiber optic cables, to a spectrometer that may be housed within the inspection head 110 (not shown). The collected light energy is analyzed by the spectrometer according to predetermined criteria. The information generated by the spectrometer is then forwarded via a data cable 140 to a computer 135 for display, storage, or further analysis. The computer 135 may be preloaded with processing information pertaining to the specific packaging or inspection operation being conducted. The information gathered about the tablets 130 contained in each package 125 may then be used to determine whether the specific tablets being inspected conform with a predetermined quality criteria.

By gathering spectrographic data about each of the tablets 130, a determination can be made as to whether the packages have been properly filled or contain the proper product. Spectrographic analysis also allows other determinations to be made that are not available with known vision-based systems, such as proper pharmacological composition, water content, and other chemical and physical properties.

Figure 2:
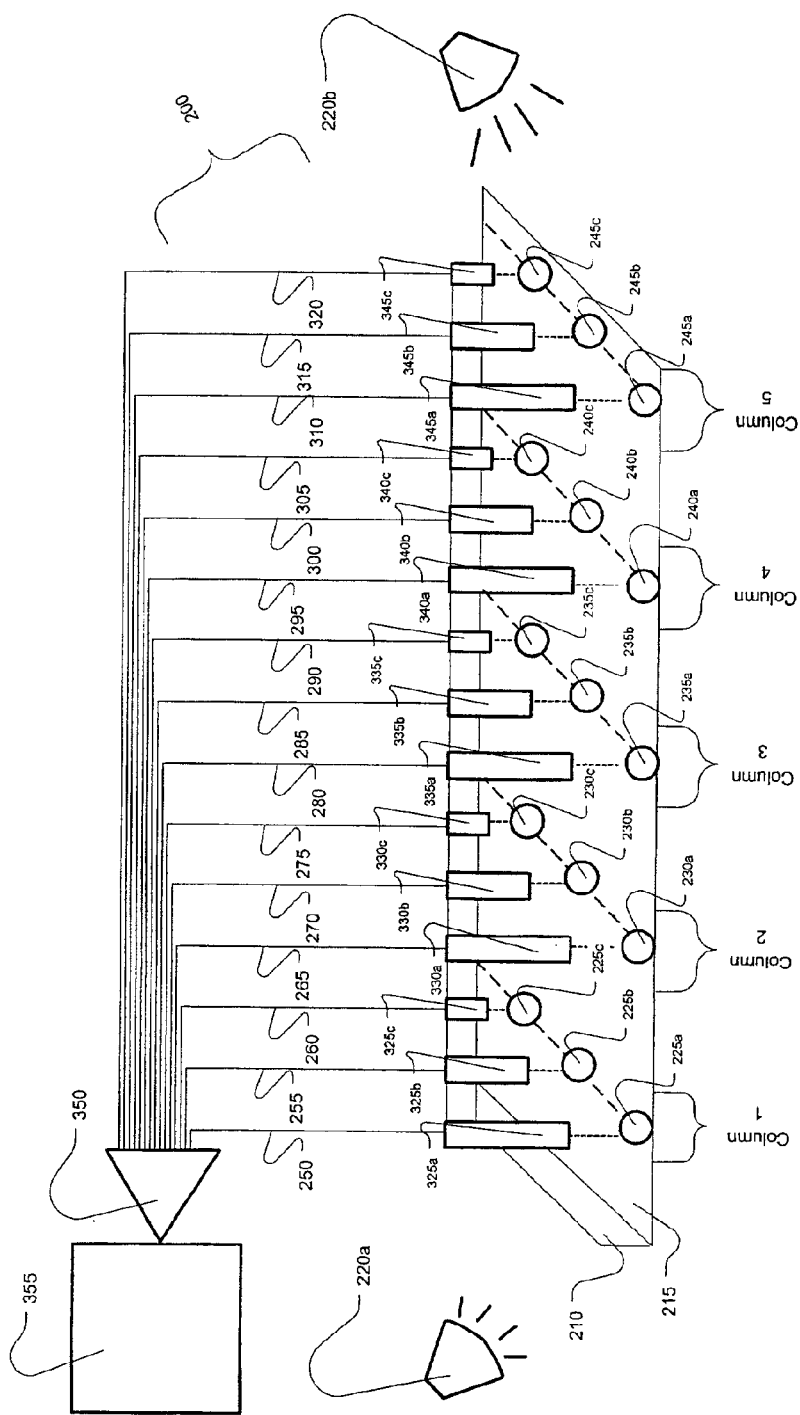
FIG. 2 is a diagram of a first embodiment of an inspection head constructed in accordance with the present invention.

FIG. 2 shows in further detail a diagrammatic representation of a lower portion of the inspection head 110, and more particularly, the array of sample probes and how they interact with the tablets passing along the conveyer 120. The probe array is generally referred to in FIG. 2 as reference number 200. In the example of FIG. 2, a product package 215, such as a filled but yet un-sealed blister package, contains fifteen (15) individual tablets in a three-by-five arrangement. Various other arrangements of the tablets are contemplated and the three-by-five arrangement of FIG. 2 is shown merely as an example. The tablets in the package 215 are arranged into five columns. From left to right in FIG. 2, column one includes tablets 225a, 225b, and 225c, column two contains tablets 230a, 230b, and 230c, column three contains tablets 235a, 235b, and 235c, column four contains tablets 240a, 240b, and 240c, and column five contains tablets 245a, 245b, and 245c. Corresponding to each of the fifteen tablets in FIG. 2 is a sample probe. From left to right, the sample probes also are divided into five columns with three sample probes in each column. Column one contains sample probes 325a, 325b, and 325c, column two contains sample probes 330a, 330b, and 330c, column three contains sample probes 335a, 335b, and 335c, column four contains sample probes 340a, 340b, and 340c, and column five contains sample probes 345a, 345b, and 345c. As the conveyer system moves the package 215 into position under the inspection head 110, the fifteen sample probes are positioned to correspond respectively to a similarly positioned tablet in the package 215. Namely, the sample probes are positioned substantially above the correspondingly positioned tablet.

Each of the sample probes are connected to a fiber optic cable which in turn is connected to a light energy aggregator 350. In FIG. 2, the fifteen fiber optic cables are represented as reference numbers 250, 255, 260, 265, 270, 275, 280, 285, 290, 295, 300, 305, 310, 315, and 320. Each one of the fiber optic cables corresponds to a single sample probe and thus also corresponds to a light reading from the corresponding tablet passing beneath the inspection head.

The light energy aggregator 350 operates to combine the light energy gathered by each of the fifteen sample probes (via the fiber optic cables) and output the combined light energy through a single output terminal. Further details of a preferred embodiment of a light energy aggregator constructed in accordance with the present invention are described in conjunction with FIGS. 8–12. Briefly, the combined light energy from the light energy aggregator 350 is directed to an entrance slit on a spectrometer 355 where it is subsequently analyzed. Light sources 220a and 220b illuminate the tablets as they pass beneath the sample probes.

In operation, the inspection head allows a system to evaluate whether any of the fifteen tablets in the package 215 are misplaced, defective, missing, chemically non-conforming, or have another problem, while utilizing a single spectrometer 355. As the packaging system begins a run, reflectance data is acquired from a known representative sample package of tablets as it passes beneath the tips of the sample probes, and statistics are compiled based on the combined spectra of the items being inspected. The representative package is of a known quality, and this initial run is thus classified as a calibration run. Appropriate preprocessing of the spectra such as smoothing or first or second differencing is applied. During the normal inspection process associated with a packaging run, the spectrum of each group or package of tablets is compared back to the representative spectra collected during the calibration run. This comparison may be through principal component analysis in which the first two or more eigenvectors are calculated and applied to the spectrum of each group of inspected items. Another comparison method relies on the dot product between the vector containing values from each of the spectral wavelength channels in the calibration run and the spectral vector of the package to be inspected. Any spectrum that deviates in its totality by more than a specified number of standard deviations is deemed to contain foreign material and a signal is sent to the packaging machine causing the group of items/package in question to be rejected and removed from the line before final packaging. Further details of spectra comparisons, as well as other methods of comparison, can be found in the *Handbook of Near-Infrared Analysis*, Donald Bums and Emil W. Ciurczak, Marcel Dekker, Inc. 1992, the details of which are hereby incorporated by reference into the present application. Alternately, if reflectance values are known for a particular item or package, this information can be input directly into the inspection system and a calibration run becomes unnecessary.

Figure 3:
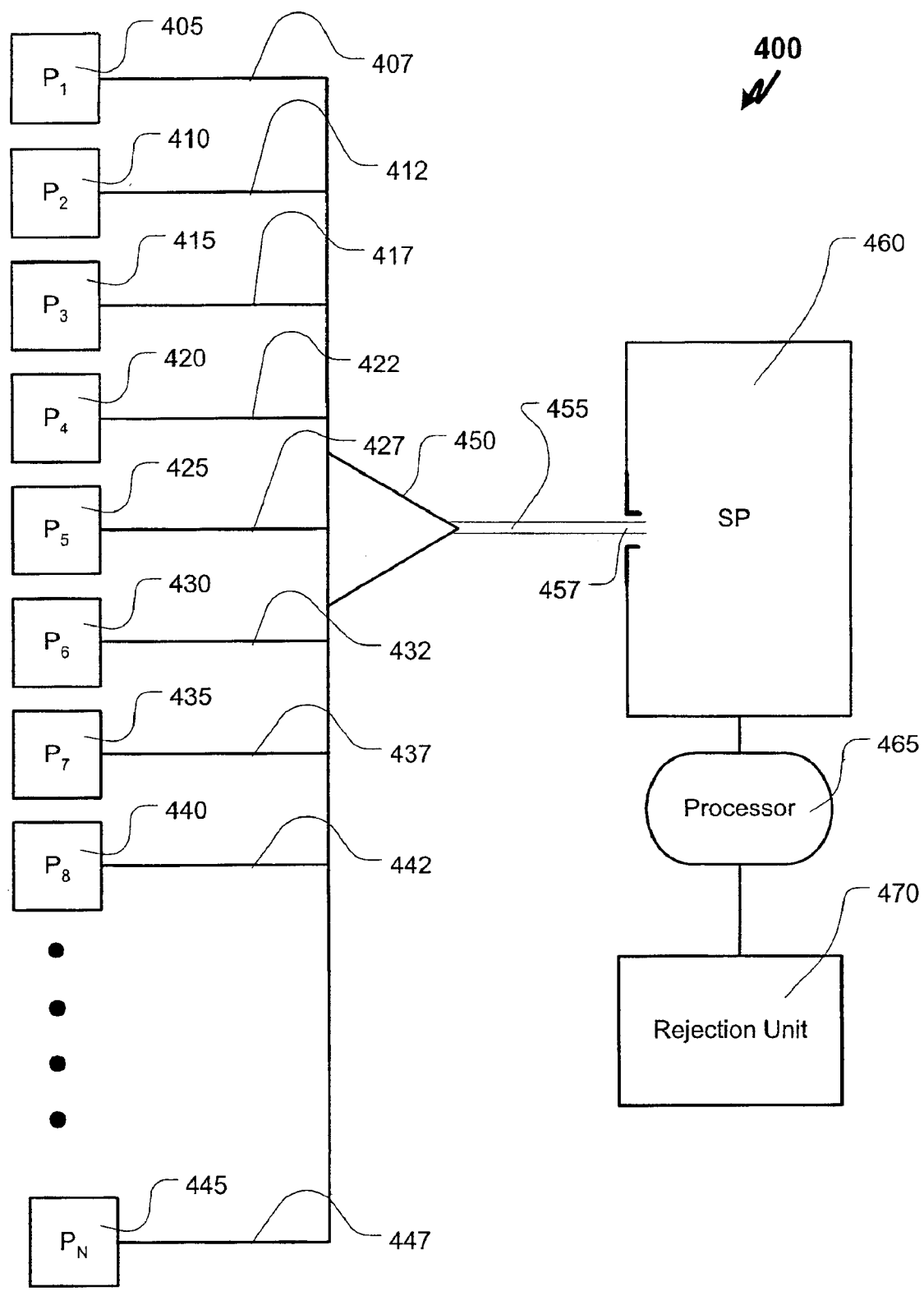
FIG. 3 is a schematic representation of the inspection head of FIG. 2.

Turning to FIG. 3, a schematic diagram of an inspection system 400 constructed in accordance with the present invention is shown. The schematic diagram of FIG. 3 generally corresponds to FIG. 2. The diagram of FIG. 3 represents how a number of different sample probes $P_1$–$P_N$ can be utilized to obtain a spectrographic measurement from any number of individual samples and feed the collected information to a single spectrometer as a combined input. Based on the combined reading from all of the sample probes, an evaluation can be made as to whether a defect (either chemical or physical) exists somewhere in the package. Since a combined value is obtained, the package as a whole is analyzed for a defect rather than each particular tablet. If the package as a whole is determined to have a defect, that entire package can be rejected. Utilizing such a system allows faster analysis while utilizing a single spectrometer thereby making the system as a whole less expensive and easier to maintain.

With continuing reference to FIG. 3, Each of the sample probes $P_1$ through $P_n$, represented by reference numbers 405, 410, 415, 420, 425, 430, 435, 440, and 445 are connected to a fiber optic cable, shown as reference numbers 407, 412, 417, 422, 427, 432, 437, 442, and 447 respectively. The fiber optic cables are, in turn, connected to a light energy aggregator 450. The light energy aggregator 450 operates to combine the light energy gathered by each of the fiber optic cables and output the combined light energy through a single output terminal. Further details of a preferred embodiment of a light energy aggregator constructed in accordance with the present invention are described in conjunction with FIGS. 8–12. Briefly, and as shown in FIG. 3, the combined output light energy from the light energy aggregator 450 is directed through a single fiber optic cable 455 and through an entrance slit 457 of a spectrometer 460. The combined light energy is subsequently analyzed by the spectrometer 460. A processor 465 is coupled to the spectrometer 460 and further analyzes the combined light energy received by the spectrometer 460. The processor 465 then compares these results to a pre-determined or pre-assigned value that represents an acceptable measurement of the package (i.e. a package without an unacceptable level of defects). The comparison value can either be obtained by a calibration run as described above or can be input into the processor based on known values. If the defect level does not conform to the comparison value, a rejection unit 470 coupled to the processor sends a signal to the packaging line to discard or remove the package with the defect.

The embodiment of the inspection system of FIGS. 2 and 3 utilizes a single spectrometer to analyze the collective samples of fifteen different sample probes and thus can reject or accept a package based on whether the package spectra as a whole meets a pre-determined criteria. As mentioned above, the use of a single spectrometer to evaluate the conformance of an entire package of tablets increases the speed of the inspection process while simultaneously reducing the cost of such an inspection system. However, the system of FIGS. 2 and 3 is unable to distinguish the precise location within the package of the foreign substance or damaged tablet. Often, it is desired to more accurately and precisely locate the non-conforming tablet(s) from within each package.

Figure 4:
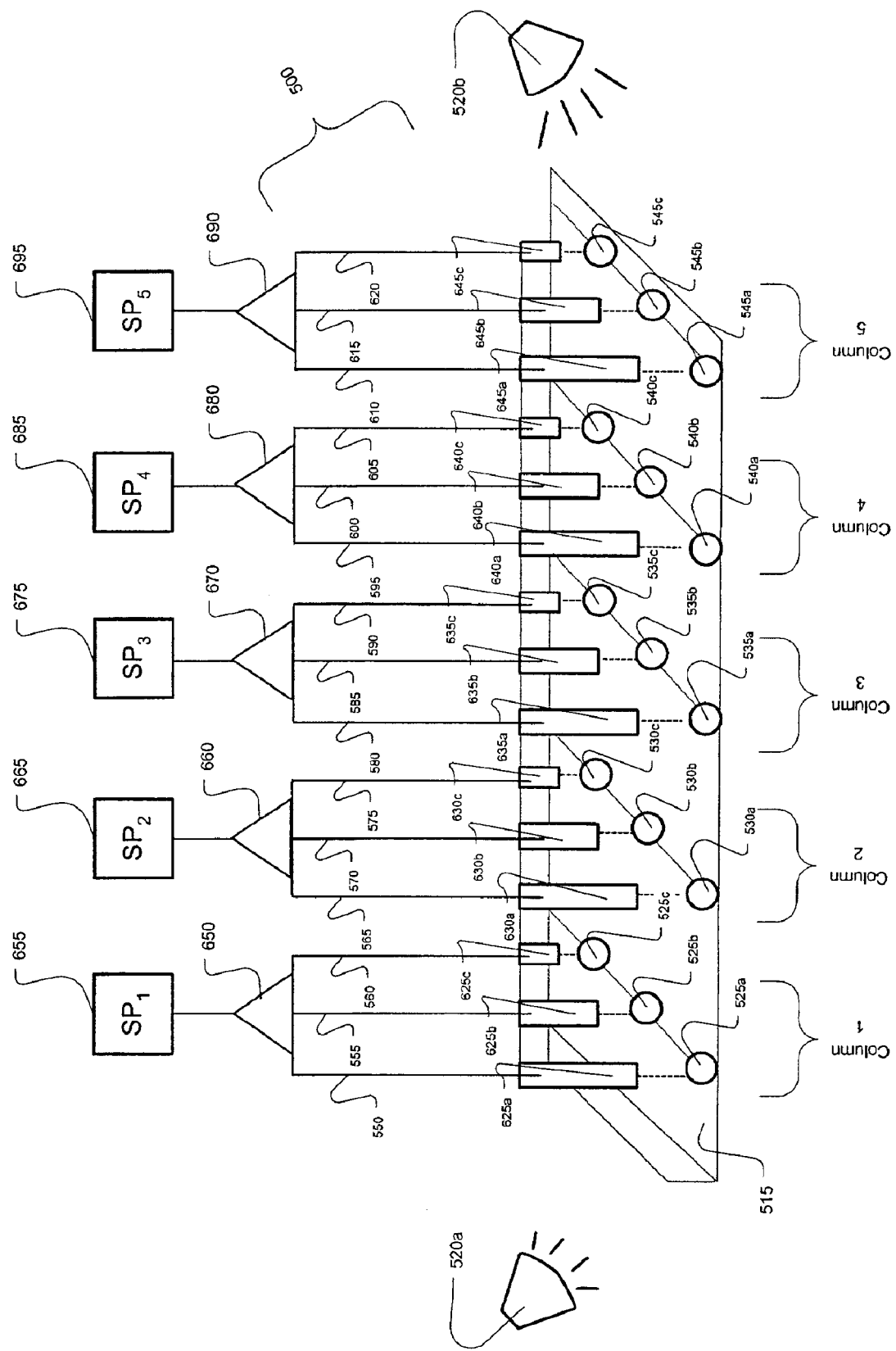
FIG. 4 is a diagram of a second embodiment of an inspection head constructed in accordance with the present invention.

Turning to FIG. 4, a diagrammatic representation of an inspection system constructed in accordance with a further aspect of the present invention is shown. FIG. 4 shows in further detail a diagrammatic representation of the lower portion of an inspection head 110 used in conjunction with an inspection system, and more particularly, an array of sample probes and how they interact with the tablets passing along a conveyer. The probe array is generally referred to in FIG. 4 as reference number 500. In the example of FIG. 4, a product package 515, such as a filled but yet un-sealed blister package, contains fifteen (15) individual tablets in a three-by-five arrangement. Various other arrangements of the tablets are contemplated and the three-by-five arrangement of FIG. 4 is shown merely as an example. The tablets in the package 215 are arranged into five rows. From left to right in FIG. 4, column one includes tablets 525a, 525b, and 525c, column two contains tablets 530a, 530b, and 530c, column three contains tablets 535a, 535b, and 535c, column four contains tablets 540a, 540b, and 540c, and column five contains tablets 545a, 545b, and 545c. Corresponding to each of the fifteen tablets in FIG. 2 is a sample probe. From left to right, the sample probes also are divided into five columns with three sample probes in each column. Column one contains sample probes 625a, 625b, and 625c, column two contains sample probes 630a, 630b, and 630c, column three contains sample probes 635a, 635b, and 635c, column four contains sample probes 640a, 640b, and 640c, and column five contains sample probes 645a, 645b, and 645c. As the conveyer system moves the package 515 into position under the inspection head 110, the fifteen sample probes are positioned to correspond respectively to a similarly positioned tablet in the package 515. Namely, the samples probes are positioned substantially above the correspondingly positioned tablet.

Each of the sample probes are connected to a fiber optic cable which in turn is connected to one of five different light energy aggregators 650, 660, 670, 680, or 690. In FIG. 4, the fifteen fiber optic cables are represented as reference numbers 550, 555, 560, 565, 570, 575, 580, 585, 590, 595, 600, 605, 610, 615, and 620. Each one of the fiber optic cables corresponds to a single sample probe and thus also corresponds to a light reading from the corresponding tablet passing beneath the inspection head.

Each of the light energy aggregators 650, 660, 670, 680, and 690 operates to combine the light energy gathered by the three sample probes (via the fiber optic cables) that feed light energy into it. Each light energy aggregator then outputs the combined light energy through a single output terminal. In the embodiment of FIG. 4, each of the light energy aggregators 650, 660, 670, 680, and 690 is associated with the fiber optic cables and sample probes from a single column. More specifically, light energy aggregator 650 receives light energy input from fiber optic cables 550, 555, and 560, light energy aggregator 660 receives light energy input from fiber optic cables 565, 570, and 575, light energy aggregator 670 receives light energy input from fiber optic cables 580, 585, and 590, light energy aggregator 680 receives light energy input from fiber optic cables 595, 600, and 605, and light energy aggregator 690 receives light energy input from fiber optic cables 610, 615, and 620. Further details of a preferred embodiment of a light energy aggregator constructed in accordance with the present invention are described in conjunction with FIGS. 8–12. Briefly, the combined light energy from each of the light energy aggregator's 650, 660, 670, 680, and 690 is directed to an entrance slit on a corresponding spectrometer 655, 665, 675, 685, or 695 where it is subsequently analyzed. Light sources 520a and 520b illuminate the tablets as they pass beneath the sample probes.

In operation, the inspection head allows a system to evaluate whether one or more of the fifteen tablets in the package 515 are misplaced, defective, missing, chemically non-conforming, or otherwise non-conforming. As the packaging system begins a run, reflectance data is acquired from a known representative sample package of tablets as they pass beneath the tips of the sample probes and statistics are compiled based on the combined spectra of the items being inspected. The representative package is of a known quality and this initial run is thus classified as a calibration run. Preprocessing of the spectra is applied in a similar manner as described above in conjunction with FIG. 2, however, information is gathered on a column-by-column basis rather than on a whole-package-basis as in the embodiment of FIG. 2. In this manner, if a defect or other abnormality is discovered within the package 515, the location of the defect can be narrowed down to a particular column within the package allowing segregation of the defective component and allowing more of the conforming tablets to be reused in the packaging run. Less waste and higher throughput is therefore realized.

Similarly, where blister packs contain more than one formulation, e.g. the package in FIG. 4 could have up to 5 formulations (one in each row), the system would be able to detect a misplaced tablet in any of the columns. Single spectrometer systems would not be able to detect when a tablet in one row got inadvertently switched with a tablet in a second row having a different formulation. Probes from the multiple spectrometer system of FIG. 4 can be arranged in any configuration and not just in rows as shown.

Figure 5:
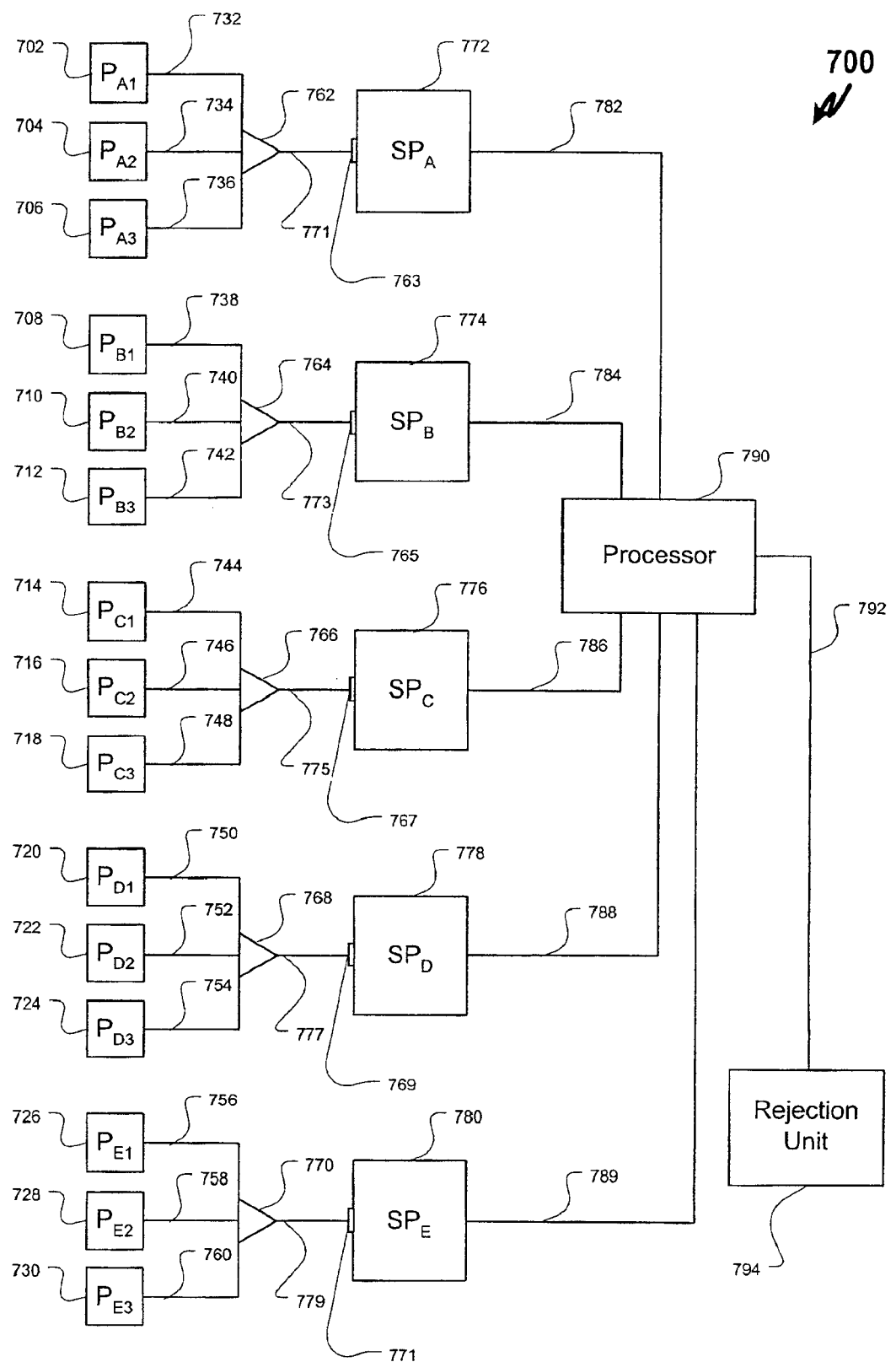
FIG. 5 is a schematic representation of the inspection head of FIG. 4.

Turning to FIG. 5, a schematic diagram of an inspection system 700 constructed in accordance with the present invention is shown. The schematic diagram of FIG. 5 generally corresponds to FIG. 4. The diagram of FIG. 5 represents how a number of different sample probes $P_{A1}$–$P_{E3}$ can be utilized to obtain a spectrographic measurement from any number of individual samples on a column-by-column basis and feed the collected column-by-column information through a column specific light energy aggregator to a column-specific spectrometer as a combined input. Based on the combined reading from the sample probes in each row, an evaluation can be made as to whether a defect (either chemically or physically) exists somewhere in the package. In the case of a blister package containing tablets with several different formulations, groups of probes feeding light to each of the light energy aggregators are positioned above the groups of tablets having a single formulation. A further determination can be made as to which column the defect or other abnormality resides. Since a combined value is obtained for each column of tablets, a particular column as a whole is analyzed for a defect rather than each particular tablet. Thus, the system can detect when tablets with a given formulation are placed in the wrong row. In many cases, any such formulation misplacement will cause the entire package to be rejected, however, it is contemplated that the otherwise conforming tablets can be salvaged and stored for later reuse or can be automatically placed back into the packaging line for inclusion in a subsequent package. Utilizing such a system allows faster analysis while requiring a fewer number of spectrometers thereby making the system as a whole less expensive and easier to maintain.

With continuing reference to FIG. 5, each of the sample probes $P_{A1}$ through $P_{E3}$, represented by reference numbers 702, 704, 706, 708, 710, 712, 714, 716, 718, 720, 722, 724, 726, 728, and 730 are connected to a corresponding fiber optic cable, shown as reference numbers 732, 734, 736, 738, 740, 742, 744, 746, 748, 750, 752, 754, 756, 758, and 760 respectively. The subscript designation in each of the probe labels refers to the column and row of each sample probe respectively. Namely, the letter designations, A, B, C, etc. refer to the first, second, third, etc. columns while the number designations 1, 2, and 3, refer to the row designation in each column. Each one of the array of fifteen sample probes can therefore be uniquely represented.

The column-by-column groupings of fiber optic cables are in turn connected to a corresponding light energy aggregator 762, 764, 766, 768, or 770. Each of the light energy aggregators operate to combine the light energy gathered by the fiber optic cables from a particular column and output the combined light energy through a single output terminal. Further details of a preferred embodiment of a light energy aggregator constructed in accordance with the present invention are described in conjunction with FIGS. 8–12. Briefly, and as shown in FIG. 5, the combined output light energy from the light energy aggregator 762 is directed through a single fiber optic cable 771 and through an entrance slit 763 of a spectrometer 772. The combined light energy is subsequently analyzed by the spectrometer 772. The combined output light energy from the light energy aggregator 764 is directed through a single fiber optic cable 773 and through an entrance slit 765 of a spectrometer 774. The combined light energy is subsequently analyzed by the spectrometer 774. The combined output light energy from the light energy aggregator 766 is directed through a single fiber optic cable 775 and through an entrance slit 767 of a spectrometer 776. The combined light energy is subsequently analyzed by the spectrometer 776. The combined output light energy from the light energy aggregator 768 is directed through a single fiber optic cable 777 and through an entrance slit 769 of a spectrometer 778. The combined light energy is subsequently analyzed by the spectrometer 778. The combined output light energy from the light energy aggregator 770 is directed through a single fiber optic cable 779 and through an entrance slit 781 of a spectrometer 780. The combined light energy is subsequently analyzed by the spectrometer 780.

A processor 790 is coupled to each of the five spectrometers 772, 774, 776, 778, and 780 by data cables 782, 784, 786, 788, and 789 and further analyzes the combined light energy received by the spectrometers. The processor 790 then compares these results to a predetermined or pre-assigned value that represents an acceptable measurement of the package (i.e. a package with an acceptable level of defects). The comparison value can either be obtained by a calibration run as described above or can be input into the processor based on known values. If the defect level does not conform to the comparison value, a rejection unit 794 coupled to the processor sends a signal to the packaging line to discard or remove the package with the defect.

Figure 6:
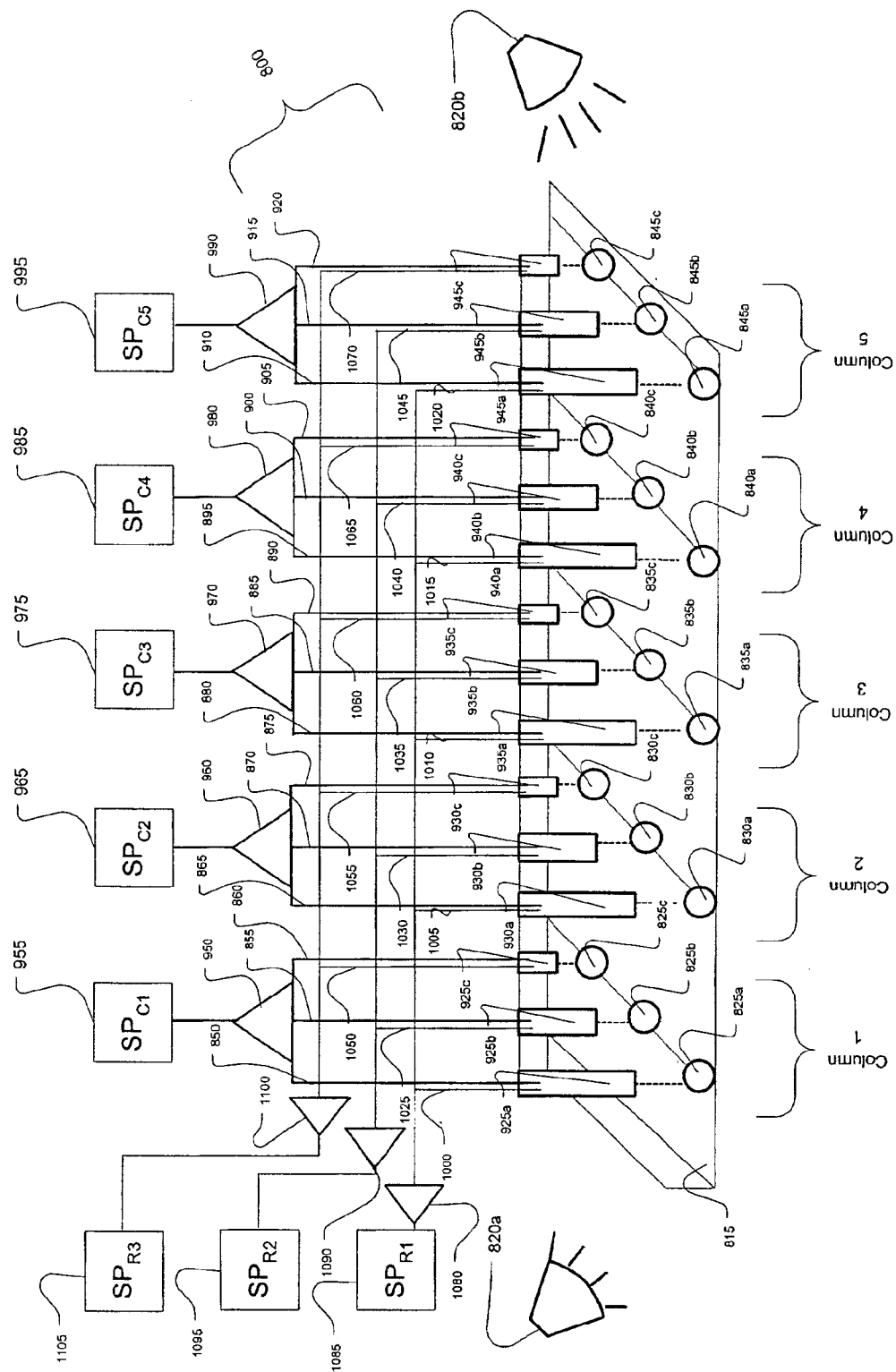
FIG. 6 is a diagram of a further embodiment of an inspection head constructed in accordance with the present invention.

Turning to FIG. 6, a diagrammatic representation of a further aspect of an inspection system constructed in accordance with the present invention is shown. FIG. 6 shows in further detail a diagrammatic representation of the lower portion of an inspection head 110 used in conjunction with an inspection system, and more particularly, an array of sample probes and how they interact with the tablets passing along a conveyer. The probe array is generally referred to in FIG. 6 as reference number 800. In the example of FIG. 6, a product package 815, such as a filled but yet un-sealed blister package, contains fifteen (15) individual tablets in a three-by-five arrangement. Various other arrangements of the tablets are contemplated and the three-by-five arrangement of FIG. 6 is shown merely as an example. The tablets in the package 815 are arranged into five columns, each having three rows. From left to right in FIG. 6, column one includes tablets 825a, 825b, and 825c, column two contains tablets 830a, 830b, and 830c, column three contains tablets 835a, 835b, and 835c, column four contains tablets 840a, 840b, and 840c, and column five contains tablets 845a, 845b, and 845c. Corresponding to each of the fifteen tablets in the example of FIG. 6 is a sample probe. From left to right, the sample probes are also divided into five columns with three sample probes in each column. Column one contains sample probes 925a, 925b, and 925c, column two contains sample probes 930a, 930b, and 930c, column three contains sample probes 935a, 935b, and 935c, column four contains sample probes 940a, 940b, and 940c, and column five contains sample probes 945a, 945b, and 945c. As the conveyer system moves the package 815 into position under the inspection head 110, the fifteen sample probes are positioned to correspond respectively to a similarly positioned tablet in the package 815. Namely, the samples probes are positioned substantially above the correspondingly positioned tablet.

Each of the sample probes are connected to a pair of fiber optic cables which in turn are connected to one of five different column light energy aggregators 950, 960, 970, 980, or 990 and to one of three different row light energy aggregators 1080, 1090, or 1100. Thus, each sample probe is connected to one column light energy aggregator and to one row light energy aggregator. In FIG. 6, the thirty fiber optic cables connecting the sample probes to the eight light energy aggregator are represented as reference numbers 850, 855, 860, 865, 870, 875, 880, 885, 890, 895, 900, 905, 910, 915, 920 (corresponding to the column light energy aggregators), 1000, 1005, 1010, 1015, 1020, 1025, 1030, 1035, 1040, 1045, 1050, 1055, 1060, 1065, and 1070 (corresponding to the row light energy aggregators). Each one of these thirty fiber optic cables corresponds to a single sample probe and thus also corresponds to a light reading from a single tablet passing beneath the inspection head. Since there are two fiber optic cables for each sample probe, a reading from a particular sample probe is passed to both a column light energy aggregator and to a row light energy aggregator.

Each of the light energy aggregators 950, 960, 970, 980, 990, 1080, 1090, and 1100 operate to combine the light energy gathered by the sample probes (via the fiber optic cables) that feed light energy into it. Each light energy aggregator then outputs the combined light energy through a single output terminal. In the embodiment of FIG. 6, each of the light energy aggregators 950, 960, 970, 980, and 990 is associated with the fiber optic cables and sample probes from a single column, while each of the light energy aggregators 1080, 1090, and 1100 is associated with the fiber optic cables and sample probes from a single row. More specifically, light energy aggregator 950 receives light energy input from fiber optic cables 850, 855, and 860, light energy aggregator 960 receives light energy input from fiber optic cables 865, 870, and 875, light energy aggregator 970 receives light energy input from fiber optic cables 880, 885, and 890, light energy aggregator 980 receives light energy input from fiber optic cables 895, 900, and 905, and light energy aggregator 9 90 receives light energy input from fiber optic cables 910, 915, and 920. Light energy aggregator 1080 receives light energy input from fiber optic cables 1000, 1005, 1010, 1015, and 1020, light energy aggregator 1090 receives light energy input from fiber optic cables 1025, 1030, 1035, 1040, and 1045, and light energy aggregator 1100 receives light energy input from fiber optic cables 1050, 1055, 1060, 1065, and 1070.

Further details of a preferred embodiment of a light energy aggregator constructed in accordance with the present invention are described in conjunction with FIGS. 8–12. Briefly, the combined light energy from each of the light energy aggregators 950, 960, 970, 980, 990, 1080, 1090, and 1100 is directed to an entrance slit on a corresponding spectrometer 955, 965, 975, 985, 995, 1085, 1095, or 1105 where it is subsequently analyzed. Light sources 820a and 820b illuminate the tablets as they pass beneath the sample probes.

In operation, the inspection head allows a system to evaluate whether one of the fifteen tablets in the package 815 are misplaced, defective, missing, chemically non-conforming, or has another problem. As the packaging system begins a run, reflectance data is acquired from a known representative sample package of tablets as they pass beneath the tips of the sample probes and statistics are compiled based on the combined spectra of the items being inspected. The representative package is of a known quality and this initial run is thus classified as a calibration run. Preprocessing of the spectra is applied in a similar manner as described above in conjunction with FIG. 2, however, information is gathered on a column-by-column and row-by-row basis rather than on a whole-package-basis as in the embodiment of FIG. 2. In this manner, if a defect or other abnormality is discovered within the package 815, the location of the defect can be narrowed down to a particular row and a particular column within the package allowing precise segregation of the defective component and allowing all of the conforming tablets to be utilized in a subsequent packaging run. Less waste and higher throughput is therefore realized.

Figure 7:
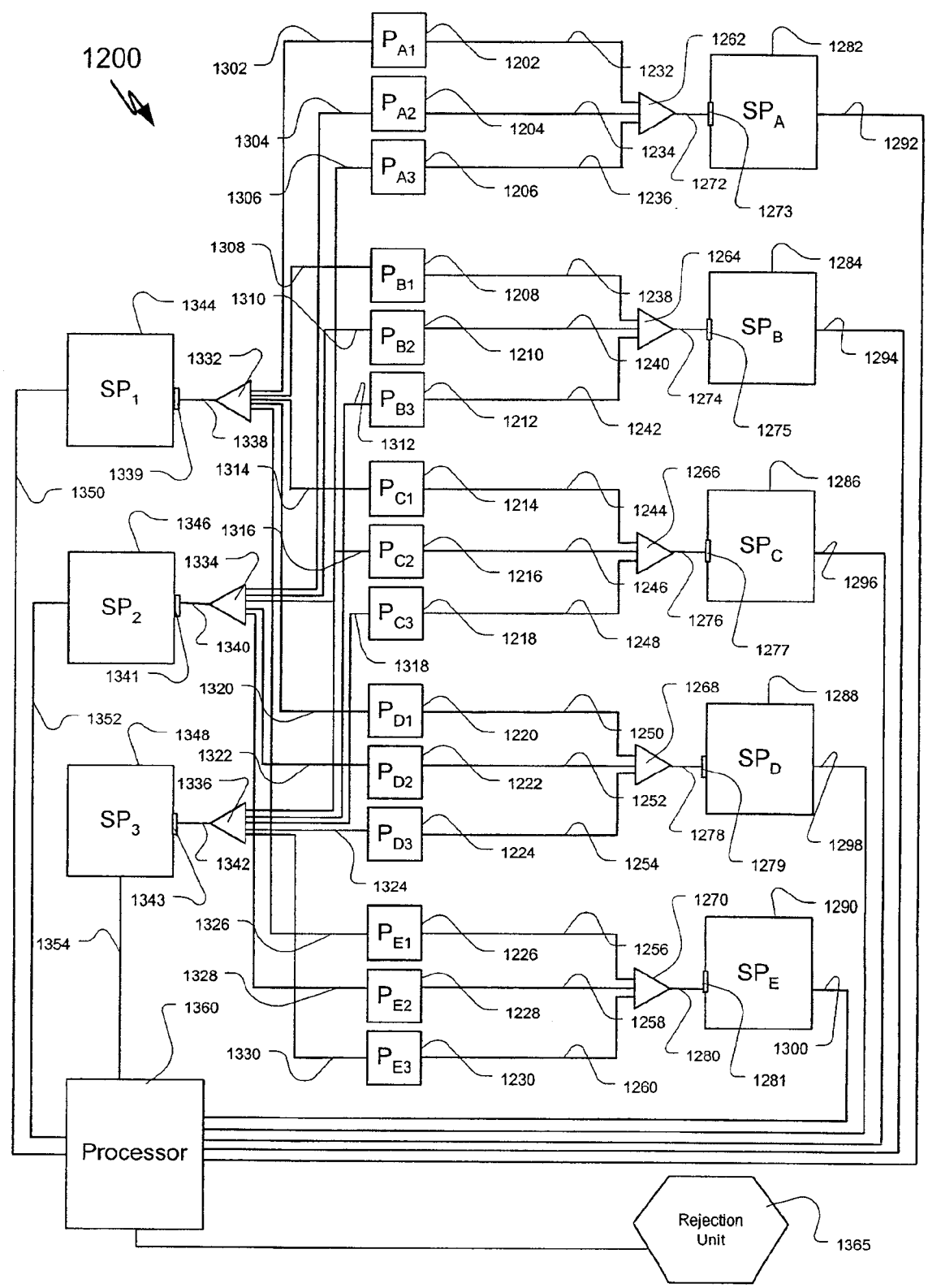
FIG. 7 is a schematic representation of the inspection head of FIG. 6.

Turning to FIG. 7, a schematic diagram of an inspection system 1200 constructed in accordance with the present invention is shown. The schematic diagram of FIG. 7 generally corresponds to FIG. 6. The diagram of FIG. 7 represents how a number of different sample probes $P_{A1}$–$P_{E3}$ can be utilized to obtain a spectrographic measurement from any number of individual samples on a row-by-row and column-by-column basis. The collected row information is fed through a row specific light energy aggregator to a row-specific spectrometer as a combined input and the collected column information is fed through a column specific light energy aggregator to a column-specific spectrometer as a combined input. Based on the combined reading from the sample probes corresponding to each row and the sample probes corresponding to each column, an evaluation can be made as to whether a defect (either chemical or physical) exists somewhere in the package. A further determination can be made as to which row and column the defect or other abnormality resides, and therefore, the precise location of the non-conforming item can be ascertained. Since a combined value is obtained for each row and column of tablets, a particular row as a whole or a particular column as a whole is analyzed for a defect rather than each particular tablet. If a particular row or particular column as a whole is determined to have a defect, the entire package can be rejected but the conforming tablets can be salvaged and stored for later reuse or be automatically placed back into the packaging line for insertion into a subsequent package. Utilizing such a system allows faster analysis while utilizing a fewer number of spectrometers thereby making the system as a whole less expensive and easier to maintain.

With continuing reference to FIG. 7, each of the fifteen sample probes $P_{A1}$ through $P_{E3}$, represented by reference numbers 1202, 1204, 1206, 1208, 1210, 1212, 1214, 1216, 1218, 1220, 1222, 1224, 1226, 1228, and 1230 are connected to a pair of corresponding fiber optic cables. The fiber optic cables corresponding to the five columns of sample probes are shown as reference numbers 1232, 1234, 1236, 1238, 1240, 1242, 1244, 1246, 1248, 1250, 1252, 1254, 1256, 1258, and 1260 respectively. The fiber optic cables corresponding to the three rows of sample probes are shown as reference numbers 1302, 1304, 1306, 1308, 1310, 1312, 1314, 1316, 1318, 1320, 1322, 1324, 1326, 1328, and 1330 respectively. The subscript designation in each of the probe labels refer to the column and row of each probe. Namely, the letter designations, A, B, C, etc. refer to the first, second, third, etc. columns and the number designations 1, 2, and 3 refer to the row designation in each column. Each of the array of fifteen sample probes can thus be uniquely represented.

The column-by-column grouping of fiber optic cables are connected to a corresponding column light energy aggregator 1262, 1264, 1266, 1268, and 1270, and the row-by-row groupings of fiber optic cables are in turn connected to a corresponding row light energy aggregator 1332, 1334, and 1336. Each of the light energy aggregators operate to combine the light energy gathered by the fiber optic cables from a particular column or row and output the combined light energy through a single output terminal. Further details of a preferred embodiment of a light energy aggregator constructed in accordance with the present invention are described in conjunction with FIGS. 8–12. Briefly, and as shown in FIG. 7, the combined output light energy from the column light energy aggregator 1262 is directed through a single fiber optic cable 1272 and through an entrance slit 1273 to a spectrometer 1282. The combined light energy is subsequently analyzed by the spectrometer 1282. The combined output light energy from the column light energy aggregator 1264 is directed through a single fiber optic cable 1274 and through an entrance slit 1275 to a spectrometer 1284. The combined light energy is subsequently analyzed by the spectrometer 1284. The combined output light energy from the column light energy aggregator 1266 is directed through a single fiber optic cable 1276 and through an entrance slit 1277 to a spectrometer 1286. The combined light energy is subsequently analyzed by the spectrometer 1286. The combined output light energy from the column light energy aggregator 1268 is directed through a single fiber optic cable 1278 and through an entrance slit 1279 to a spectrometer 1288. The combined light energy is subsequently analyzed by the spectrometer 1288. The combined output light energy from the column light energy aggregator 1270 is directed through a single fiber optic cable 1280 and through an entrance slit 1281 to a spectrometer 1290. The combined light energy is subsequently analyzed by the spectrometer 1290.

Similarly, the combined output light energy from the row light energy aggregator 1332 is directed through a single fiber optic cable 1338 and through an entrance slit 1339 to a spectrometer 1344. The combined light energy is subsequently analyzed by the spectrometer 1344. The combined output light energy from the row light energy aggregator 1334 is directed through a single fiber optic cable 1340 and through an entrance slit 1341 to a spectrometer 1346. The combined light energy is subsequently analyzed by the spectrometer 1346. The combined output light energy from the row light energy aggregator 1336 is directed through a single fiber optic cable 1342 and through an entrance slit 1343 to a spectrometer 1348. The combined light energy is subsequently analyzed by the spectrometer 1348.

A processor 1360 is coupled to each of the eight spectrometers 1282, 1284, 1286, 1288, 1290, 1344, 1346, and 1348 by data cables 1292, 1294, 1296, 1298, 1300, 1350, 1352, and 1354 respectively. The processor 1360 further analyzes the combined light energy received by the spectrometers. The processor 1360 then compares these results to a pre-determined or pre-assigned value that represents an acceptable measurement of the package (i.e. a package with an acceptable level of defects). The comparison value can either be obtained by a calibration run as described above or can be input into the processor based on known values. If the defect level does not conform to the comparison value, a rejection unit 1365 coupled to the processor 1360 sends a signal to the packaging line to discard or remove the package containing the defect.

Figure 8:
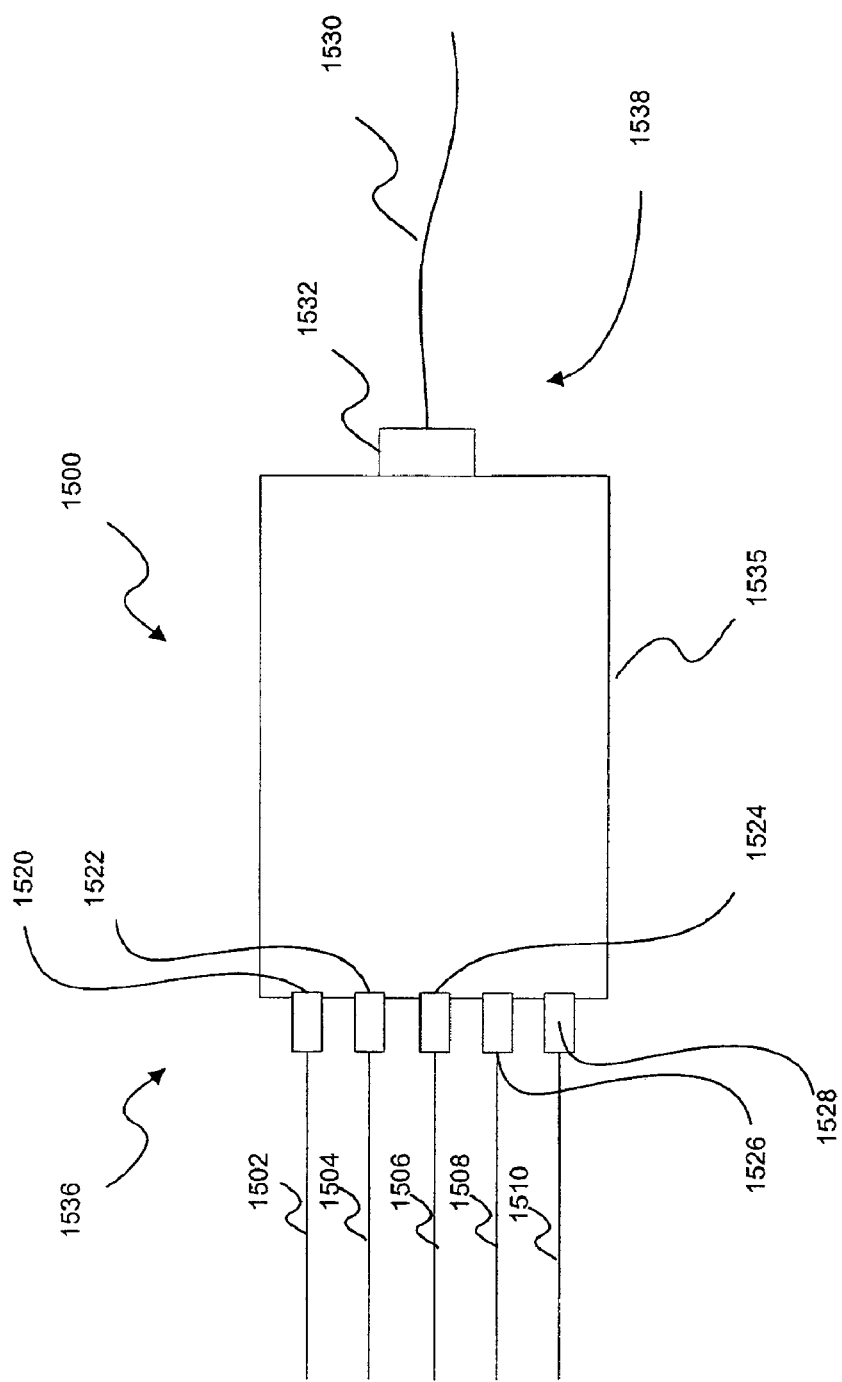
FIG. 8 is a diagram of a light energy aggregator constructed in accordance with an embodiment of the present invention.
Figure 9:
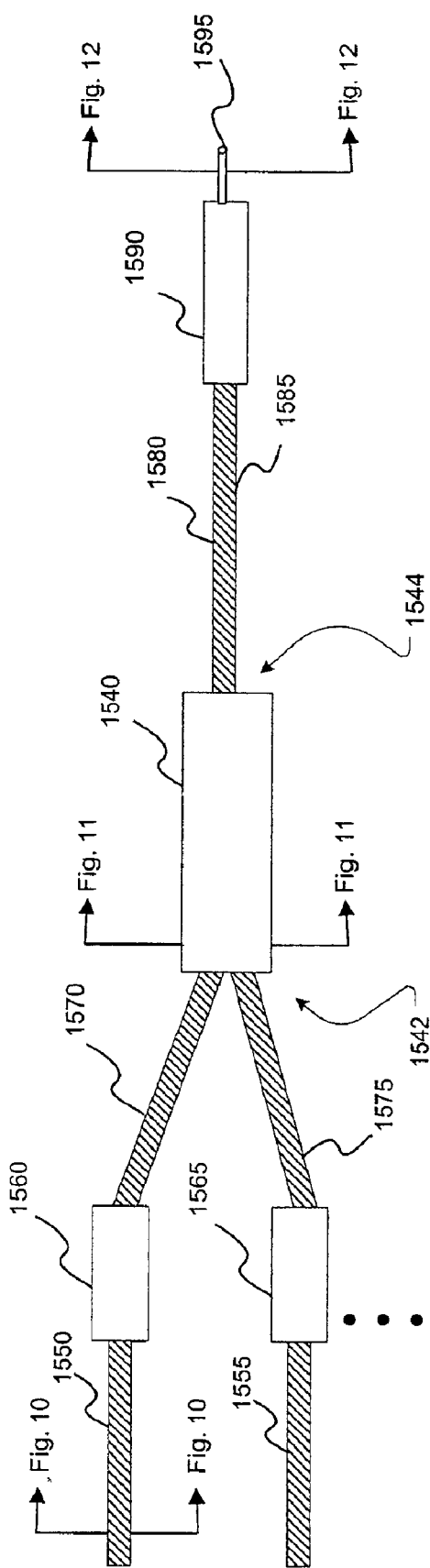
FIGS. 9–12 are details of a splitter block constructed in accordance with an embodiment of the present invention.

FIG. 8 shows a general schematic representation of a light energy aggregator 1500 utilized in an inspection system constructed in accordance with the present invention. The light energy aggregator 1500 collects the light signals transmitted by a number of fiber optic input cables, aggregates the light signals, and transmits the aggregated light signals as a single light energy output. Preferably, the light energy output represents an average reflectance value obtained through the several fiber optic input cables. The light energy aggregator 1500 includes a housing 1535 having an input end 1536 and an output end 1538. The input end 1536 includes input terminals 1520, 1522, 1524, 1526, and 1528 which connect fiber optic input cables 1502, 1504, 1506, 1508, and 1510 respectively to the light energy aggregator housing 1535. A fewer or greater number of input terminals also are contemplated. The input terminals are preferably an SMA or other type of known fiber optic connection device. The output end 1538 includes a single output terminal 1532 connected to an output fiber optic cable 1530. Alternatively, the individual light input optical fibers 1502–1510 may be combined into the single output bundle 1530 without the use of any intervening fiber optic connectors.

FIGS. 9–12 show a preferred embodiment of a light energy aggregator utilized in accordance with the present invention. The light energy aggregator embodied in FIGS. 9–12 utilizes a splitter block 1540. In conjunction with an inspection system constructed in accordance with the present invention, sample probes 1550 and 1555 take light energy readings from an item to be sampled and bring the collected light energy to the splitter block 1540. Each of the two sample probes 1550 and 1555 in FIG. 9 contain two fiber optic strands 1553 and 1554 (See cross section in FIG. 10). The fiber optic strands 1553 and 1554 are encased in an insulating and non-light transmitting material 1552. The entire probe 1550 is contained in a PVC sheathing 1551. Connection devices 1560 and 1565 connect each of the sample probes to a flexible tube 1570 or 1575 which can be directed to an input end 1542 of the splitter block 1540. While the light energy aggregator shown in FIGS. 9–12 utilizes two sample probes, it is contemplated that any number of sample probes and corresponding fiber optic strands can be utilized in an inspection system constructed in accordance with the present invention.

Again referring to FIG. 9, the splitter block 1540 includes a single bundled cable 1580 coupled to an output end 1544 of the splitter block 1540. The cable 1580 leads to a spectrometer connector 1590 having a spectrometer input tip 1595. In conjunction with the splitter block 1540, the input tip 1595 functions to bring all of the collected light energy from each of the sample probes (in this case 1550 and 1555) to a spectrometer. The input tip 1595 is therefore adapted to engage with a light entrance slit of a spectrometer.

Figure 12:
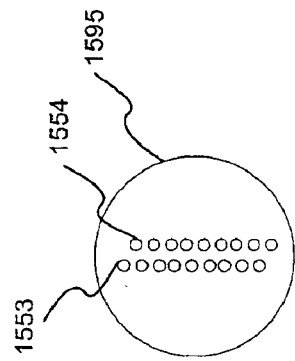
Figure 11:
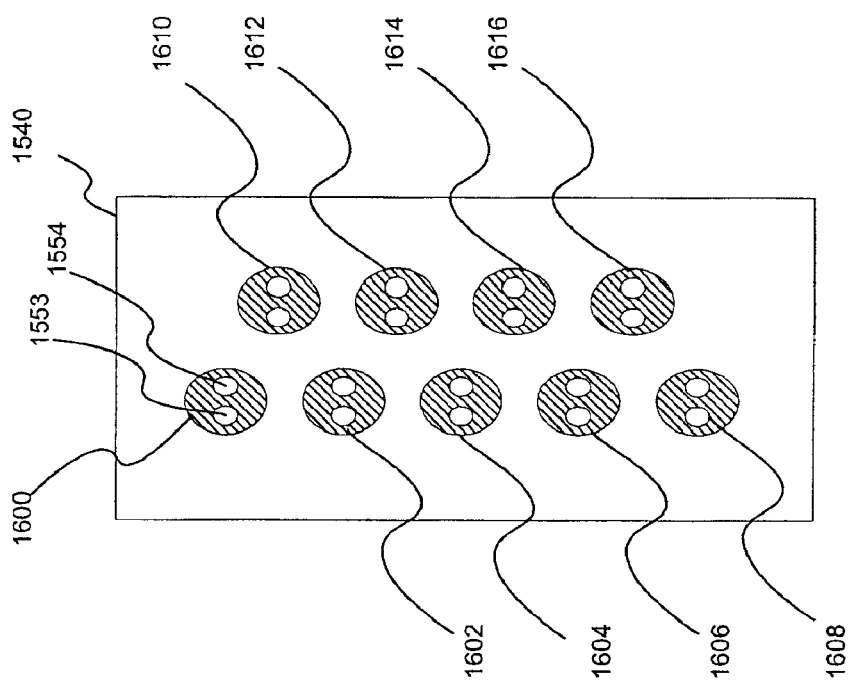
Figure 10:
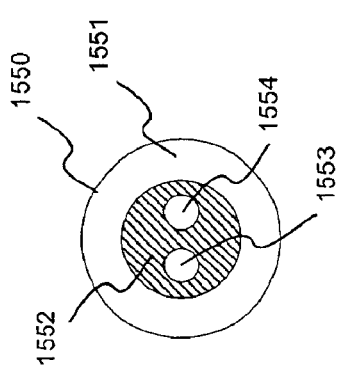

FIG. 11 shows a cross-section of the splitter block 1540. While the cross-section of FIG. 11 is representative of the splitter block shown in FIG. 9, nine probe connections are shown rather than the two embodied in FIG. 9. The nine probe connections 1600, 1602, 1604, 1606, 1608, 1610, 1612, 1614, and 1616 are substantially identical in structure, each including two separate fiber optic strands. The splitter block 1540 combines the eighteen (18) total fiber optic strands engaging the input end 1542 of the splitter block into a single bundled cable 1580 engaging the output end 1544. The bundled cable 1580 is preferably covered with a PVC sheathing 1585. FIG. 12 shows a cross section of the input tip 1595 of the bundled cable 1580 as it is adapted to align and couple with the entrance slit of a spectrometer.

The splitter block embodiment of a light energy aggregator depicted in FIGS. 9–12 is one example of such a light energy aggregator and other embodiments of a device that combines the light energy from two or more sample probes are contemplated by the present invention. For example, another embodiment of a light energy aggregator uses a reflective chamber to receive collected light energy from each of the sample probes. As all of the light energy is combined within the light chamber, a single output distributes the aggregated light energy and directs it through a single fiber optic strand. This single fiber optic strand is then directed to the entrance slit of a spectrometer. Such an embodiment of a light energy aggregator is beneficial since it reduces the complexity of the entrance slit connection. The reflective chamber is preferably highly polished, such as a gold plated finish or electro-polished stainless steel, so that light energy losses are kept to a minimum.

Figure 13:
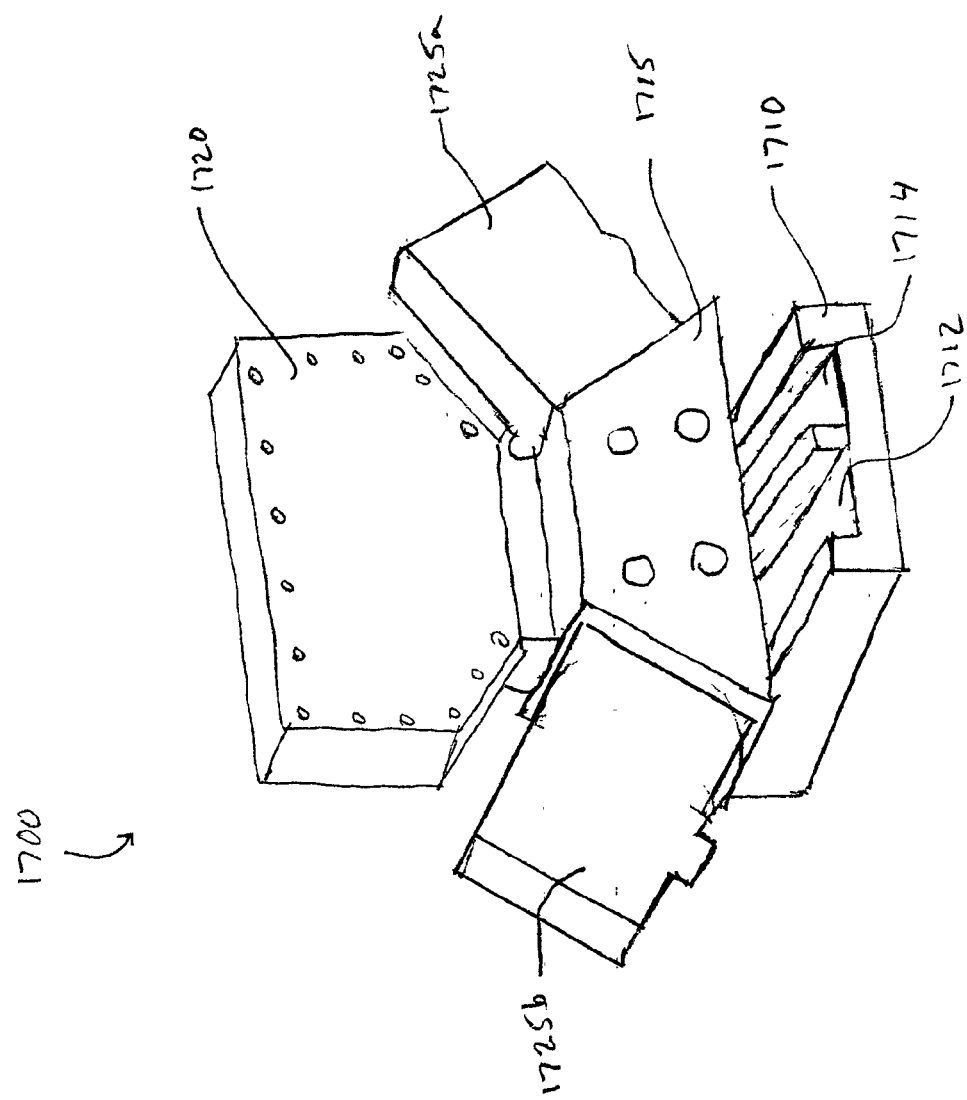
FIGS. 13–15 are perspective diagrams of an inspection head constructed in accordance with various aspects of the present invention.
Figure 14:
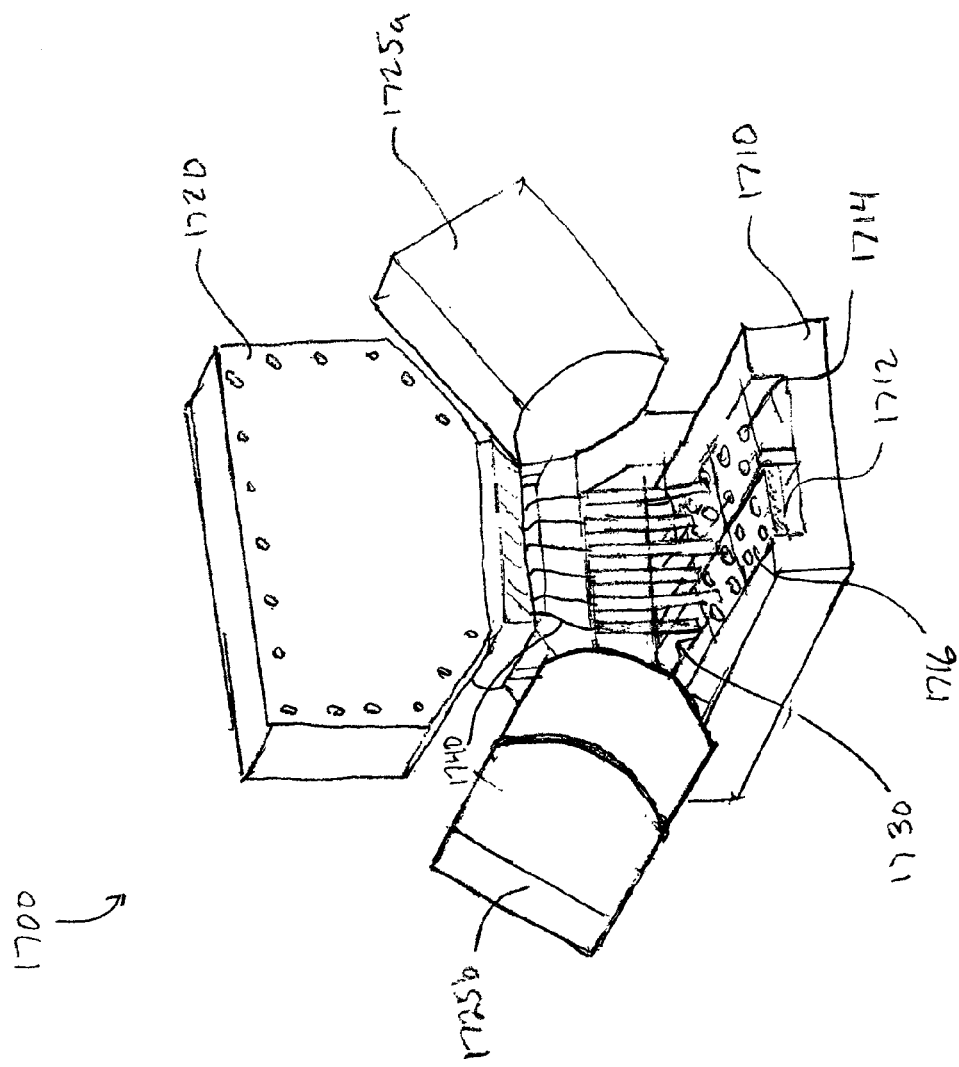
Figure 15:
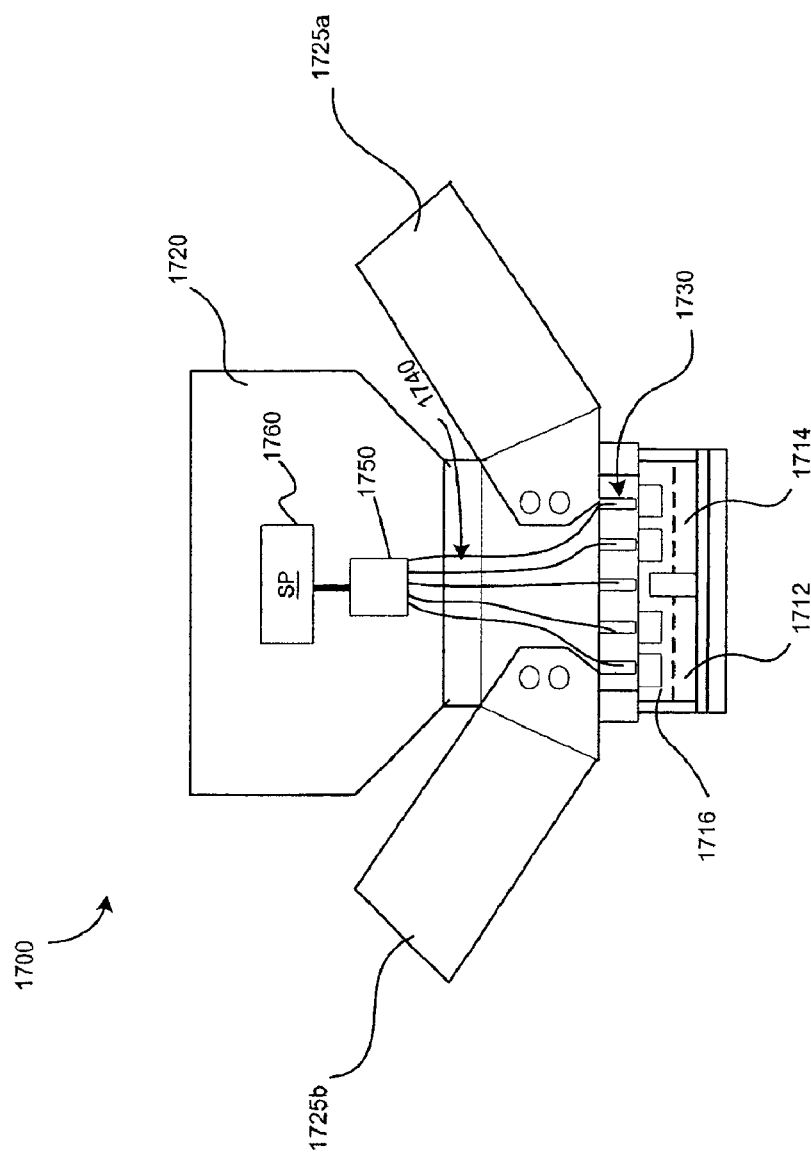

FIGS. 13–15 show a preferred embodiment of an inspection head 1700 as it mounts over a conveyer-based packaging line and inspection system. The inspection head 1700 includes a probe housing 1715 mounted over a conveyer unit 1710. The conveyer unit 1710 includes a pair of channels 1712 and 1714 that are adapted to carry, for example, filled blister packages past the inspection head 1700 and its associated sample probes. The inspection head 1700 also includes near-infrared light source housings 1725a and 1725b mounted on either side of the conveyer unit 1710. The two housings 1725a and 1725b contain a near-infrared light source that is directed at the channels 1712 and 1714 where the items to be inspected travel. It is contemplated that in other embodiments, the number of channels in the conveyer unit 1710 may be more or less than two.

In FIG. 14, a front faceplate of the probe housing is removed to illustrate the arrangement of an array of sample probes 1730. Generally, the sample probes 1730 are positioned so that they each align with a single item in a package 1716 passing beneath. FIG. 14 is shown with four individual sample probes corresponding to each of the packages 1716, since each of the packages contain four items in FIG. 14. Of course, in a system adapted to inspect packages with a different number of items, a corresponding number of sample probes would be included. Preferably, the probe housing 1715 can be easily retooled to accommodate a varying number of sample probes, for example, probe housing modules having a set number of sample probes can be utilized to easily change the format of the inspection head. Also, a probe mounting plate that has a pattern of holes for holding the probes positioned above each of the items may be utilized. The probe mounting plate may be adapted to be easily changed to accommodate a different layout of items. Pre-assembled sample probe manifolds can also be utilized to accomplish the goal of an easy exchange for use with different packaging and inspection systems that utilize varying sized packages. An array of fiber optic cables 1740 connects each of the sample probes to a spectrometer housing 1720 mounted above the sample probe housing 1715.

FIG. 15 shows a cross section of the inspection head 1700 and more particularly the connections between the sample probes 1730, the fiber optic cables 1740, a light energy aggregator 1750 and a spectrometer 1760. Preferably, the light energy aggregator 1750 and the spectrometer 1760 are both mounted within the spectrometer housing 1720 although it is contemplated that the light energy aggregator may be positioned elsewhere in the inspection head 1700. It is also contemplated that the light aggregator 1750 and/or the spectrometer 1760 may be located outside of the inspection head 1700. FIG. 15 illustrates how the sample probes 1730 align with each of the items contained in the package 1716 and combine the signal gathered by the probes in the light energy aggregator 1750. The combined signal is then transferred to the spectrometer 1760 for processing.

Figure 16:
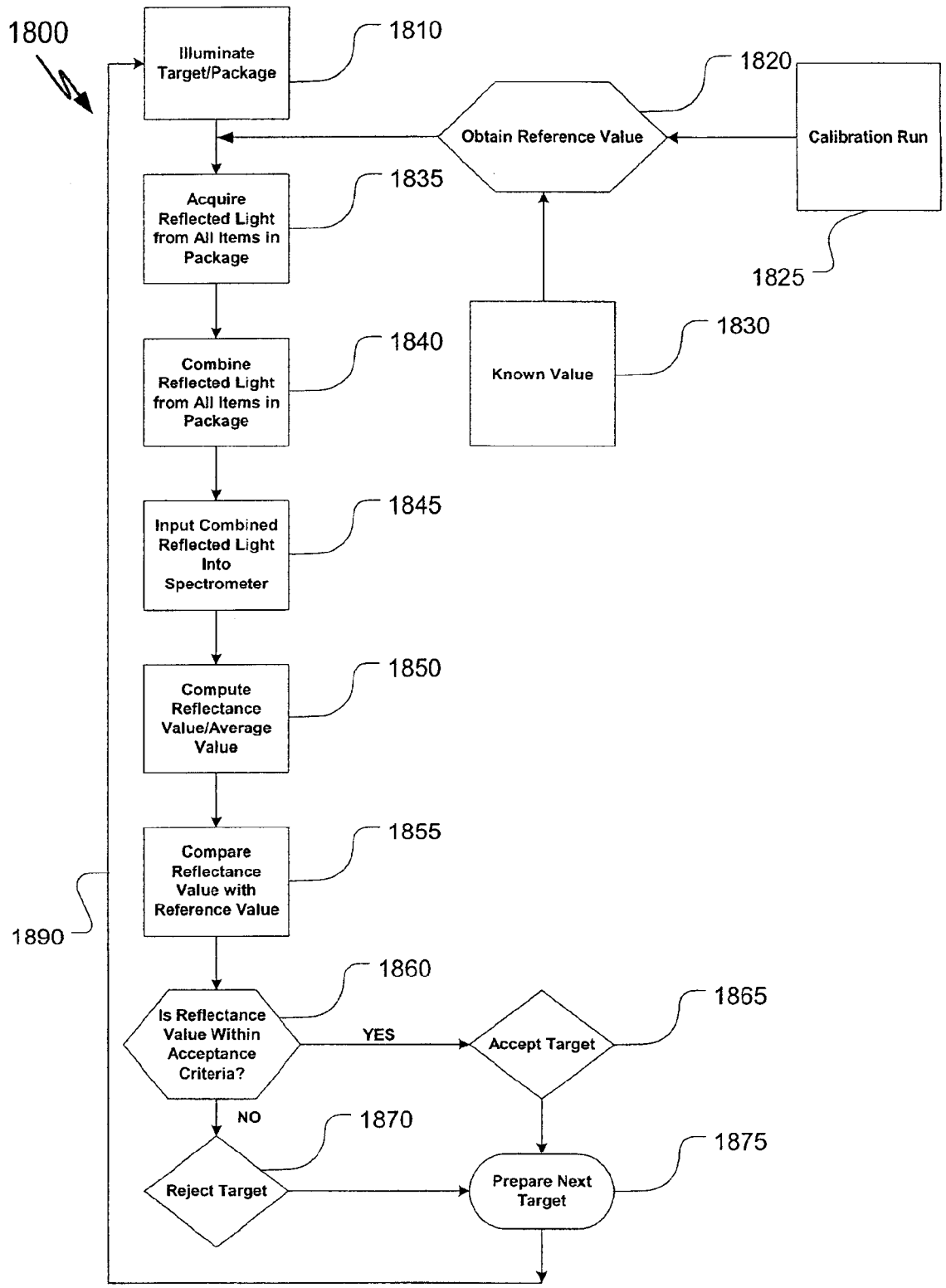
FIGS. 16 and 17 are flow charts depicting inspection methods in accordance with various embodiments of the present invention.
Figure 17:
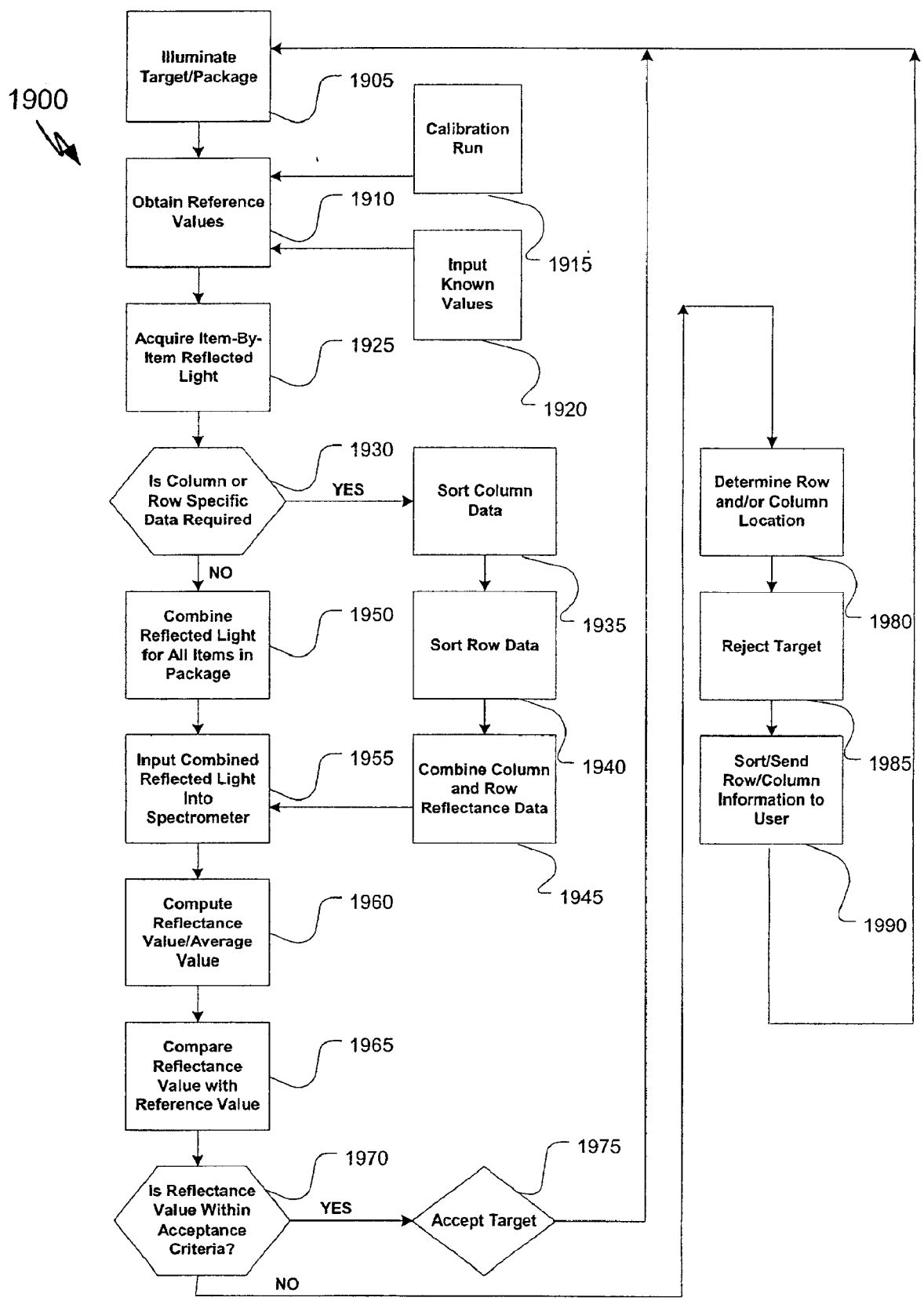

FIGS. 16 and 17 present several flow charts describing methods of inspection and analyzing reflectance data in accordance with the present invention. In FIG. 16, a method 1800 includes illuminating a target or package at 1810 and then obtaining a reference reflectance value for that package at a 1820. The reference reflectance value can be obtained either by a calibration run 1825 or by inputting the known values at 1830.

After the reference reflectance value is obtained, reflected light is collected at 1835 from all items in the target package. This reflected light is combined at 1840 and input into a spectrometer at 1845 where the light energy is measured and the reflectance calculated at 1850. A comparison is made between the reference reflectance value and the acquired reflectance value at 1855 and a determination is made at 1860 whether the acquired reflectance data falls within the reference data acceptance criteria. If the acquired reflectance data is acceptable the process continues at 1865, a next target or other sample is prepared at 1875 and the process repeats at 1890. If the acquired reflectance data is not within acceptable criteria, the target package is rejected at 1870, a next target or other sample is prepared at 1875, and the process repeats at 1890.

Turning to FIG. 17, a method 1900 includes illuminating a target or package at a 1905 and then obtaining a reference reflectance value for that package at 1910. The reference reflectance value can be obtained either by a calibration run 1915 or by inputting the known values at 1920. At 1925, item-by-item reflected light is collected, and then a determination is made at 1930 whether more detailed information about the package reflectance data is required, i.e. whether column-by-column or row-by-row reflectance data is desired. If the more detailed reflectance data is required, then the column data is sorted at 1935, the row data is sorted at 1940 and the row and column data are combined at 1945. The combined reflected light is then input into a spectrometer at 1955. If row and column specific information is not required then reflected light is combined for all of the items in the package at 1950, and the combined reflected light is input into a spectrometer at 1955.

The light energy is measured and reflectance calculated at 1960, a comparison is made between the reference reflectance value and the acquired reflectance value at 1965, and a determination is made at 1970 whether the acquired reflectance data falls within the reference data acceptance criteria. If the acquired reflectance data is acceptable the process continues at 1975, a next target is prepared for inspection, and the process repeats.

If the acquired reflectance data is not acceptable a further determination is initiated at 1980 to isolate the location of the non-conforming item or items within the package. Once the non-conforming item or items are located, the target package is rejected at 1985 and the location data is sent to a user for further processing or analysis at 1990. Alternately, the rejected package is automatically sorted and the conforming items are reinserted into the packaging system. The inspection process continues by preparing a next target for inspection and repeating the inspection process.

As mentioned above, an inspection device constructed in accordance with the present invention is preferably used in conjunction with a pharmaceutical packaging system, although it is contemplated that such an inspection system can be used with a variety of other applications such as food manufacturing/packaging, consumer goods, as well as industrial applications.

The methods and systems outlined above for inspecting and analyzing packaged items utilize an individual sample probe to collect the reflected light from each item in the package. The sample probes in the above examples and embodiments are aligned with the individual items in the package. This technique is most applicable when the location within the package of the item being analyzed is well known, such as when a standardized packaging unit is used, i.e. a blister pack for a regularly processed pharmaceutical. Other examples include oral contraceptive packaging, antihistamine packaging, and vitamin packages where multiple dosage formats are included in a single package, e.g. day and night antihistamine dosages or contraceptive dosages.

For situations where the location within the package of each item is not pre-determined, the concepts of imaging spectrometry may be utilized in accordance with an embodiment of the present invention to identify the individual item locations. In addition to identifying the item location within a package, an imaging spectrometer can be simultaneously used in accordance with an embodiment of the present invention to capture the spectrum of the individual items for analysis.

Imaging spectrometers simultaneously capture data in as many as hundreds of contiguous registered spectral bands, such that a spectral vector containing as much information as an individual spectrometer spectrum is measured for each picture element (pixel). The field of view of an imaging spectrometer may be considered as a collection of picture elements (pixels) or resolution elements (reselms). This field can be imaged onto an array of detector elements in a focal plane array (FPA), or it may be imaged by a single detector or small array that is scanned over the field. Further information and details regarding imaging spectrometers can be found in *Introduction to Imaging Spectrometers,* William L. Wolfe, 1997, wich is hereby incorporated by reference.

Generally, in a push-broom scanning-type imaging spectrometer, the spectral data is acquired one image line at a time. By moving the items to be scanned underneath the imaging element a second spatial dimension is provided, a two dimensional spatial image can be developed with a third spectral dimension. With a complete image field of a package obtained, identification and isolation of individual items within the package of items can be made by comparing the spectra obtained at each pixel with the corresponding pixel from a known background, i.e. an unfilled package. After the pixels corresponding to the filled package and the product items within the package have been isolated, any one of the analyses described above in conjunction with FIGS. 1–17 can be applied to determine whether the package items conform to a pre-determined standard.

A push broom imaging spectrometer (IS) is one that uses a 2-D detector array. One dimension of the detector is used to collect the spatial information (i.e. it images a row of spatial pixels corresponding to the various positions across the conveyor transporting the items by the head) and the other is used to collect the spectral information (i.e. each column of the array simultaneously measures the spectrum corresponding to a single spatial pixel). The image is acquired one line at a time. Optics are used to project an image of the surface under observation onto the entrance slit of the IS. The height of the entrance slit defines the height of the spatial pixels in the final image. Inside the IS, the dispersed image of the light transmitted through the entrance slit is focused onto the 2-D detector array. The wide dimension of the entrance slit is focused across the width of the detector array. Thus, the width of the detector in pixels is equal to the width of the spatial image in pixels.

The grating disperses the light perpendicular to the wide dimension of the entrance slit. Thus, the other dimension of the detector is used to collect the spectral information. The number of wavelengths measured corresponds to the dimension of the detector in this direction.

The second spatial dimension is acquired by moving the sensor relative to the surface under observation. The end result is a 3-D data set: 2 spatial and one spectral dimension.

Standard image analysis routines are used to define the centers of the items under inspection. Spectra corresponding to these center pixels (one or more pixels averaged for each item depending on the size of the item and the size of the spatial pixels) are then analyzed in the same manner as the non-IS example. Also note that because a complete image is acquired, the IS-based approach also provides the shape of the items under inspection.

Figure 18:
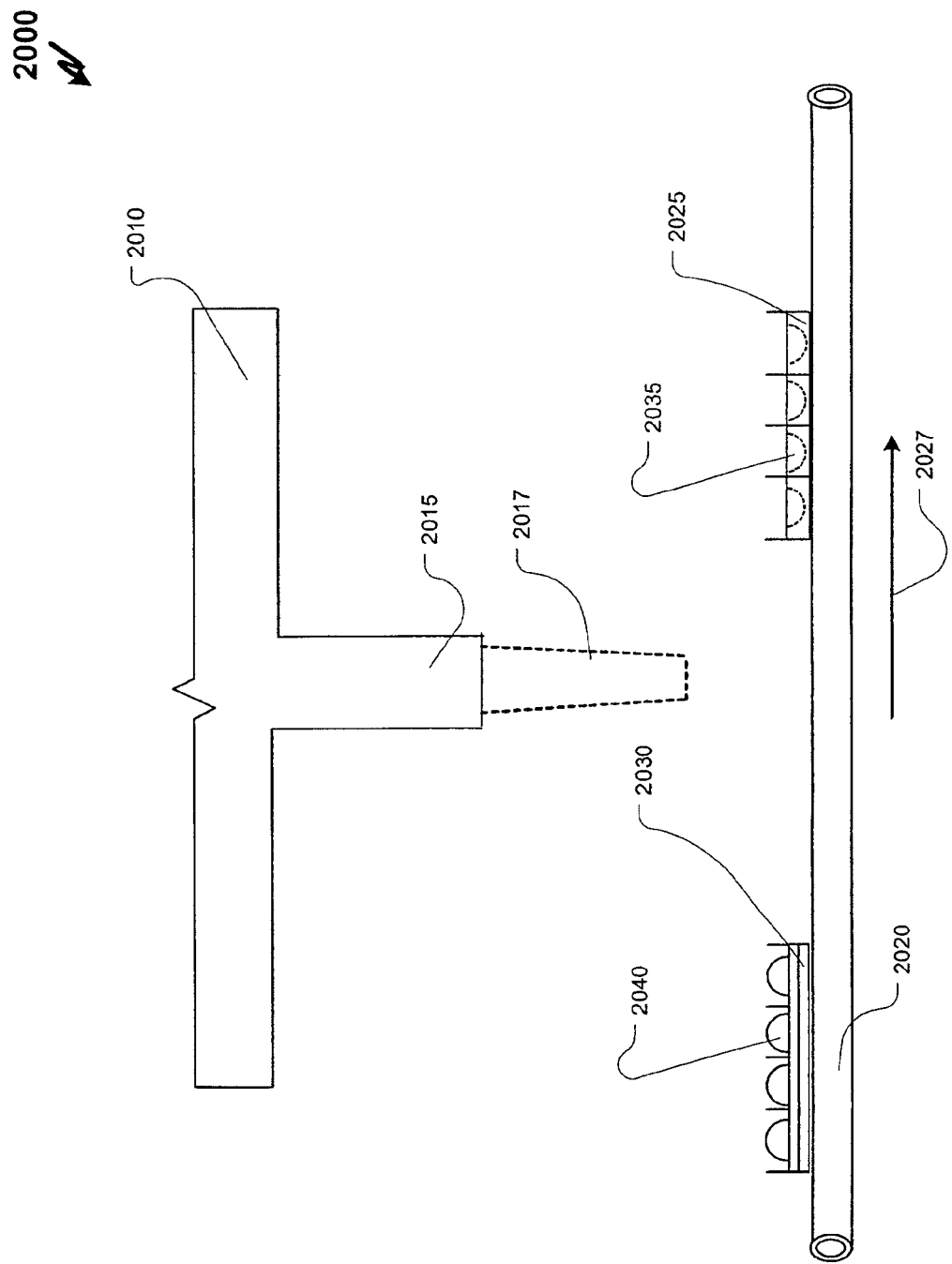
FIG. 18 is a cross-section of a scanning spectrometer system constructed in accordance with an embodiment of the present invention.

With reference to FIG. 18, a push-broom scanning imaging spectrometer system 2000 constructed in accordance with an embodiment of the present invention is shown. The imaging spectrometer system 2000 is preferably used to obtain item-location data corresponding to a package 2030 that contains, for example, an array of items 2040. As an example, the package 2030 may comprise a blister pack that includes an array of tablet wells shaped and sized to each hold an individual tablet. The spectrometer system 2000, includes an imaging spectrometer 2010 and a fore-optics unit 2015. The push broom scanning spectrometer 2000 is mounted above a conveyer system 2020 that carries the package 2030 through a field of view 2017 of the fore-optics unit 2015. The conveyer system 2020 is similar to those described in conjunction with FIGS. 1–15.

Also shown on the conveyer 2030 is an unfilled, or "blank" package 2025. The blank package 2025 in FIG. 18 also shows empty tablet wells 2035. The direction of the conveyer movement is indicated by an arrow 2027 and illustrates how the blank package 2025 passes the imaging element 2015 first, thereby providing a reference image. When the filled package 2030 passes the imaging element 2015, the spectral data gathered can be compared to the reference image previously obtained and a determination can be made as to the specific locations of the individual items 2040 within the package 2030.

Preferably, there are two reference images. The first without items in place, the second with items in place. These reference images can then be used to indicate the general location of each item with the specific location determined by standard image processing methods applied to the new image of each group of items. Alternatively, the system can use the reference image (this time only with the tablets in place) to train the system to recognize the items wherever they are located within the system's field-of-view.

Figure 19C:
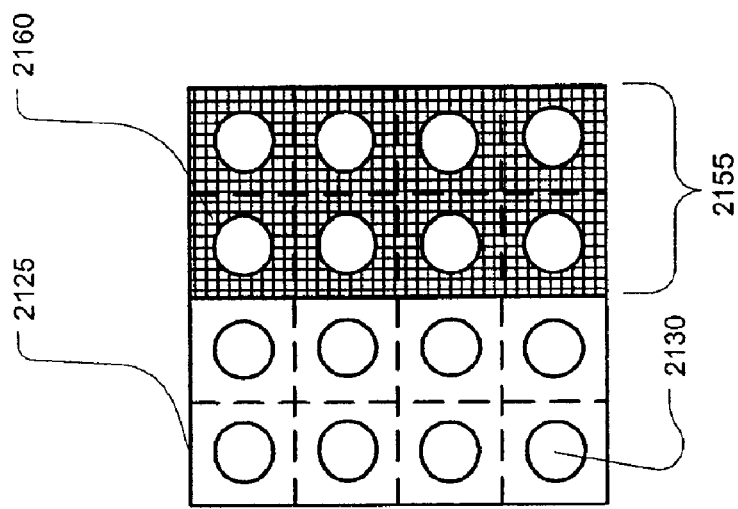
FIGS. 19A–19C are plan views of a package at various stages of an inspection system constructed in accordance with an embodiment of the present invention.
Figure 19B:
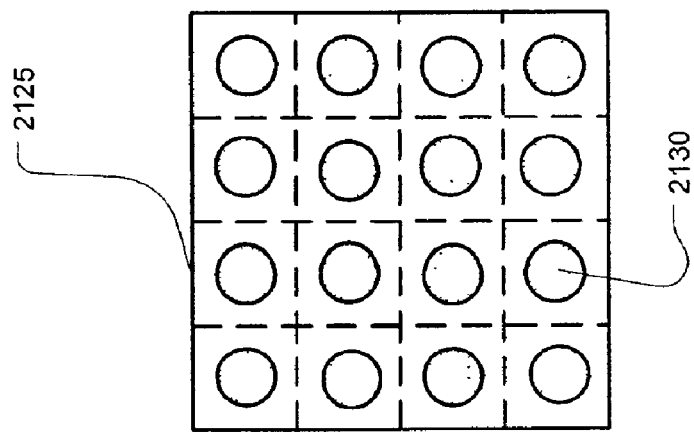
Figure 19A:
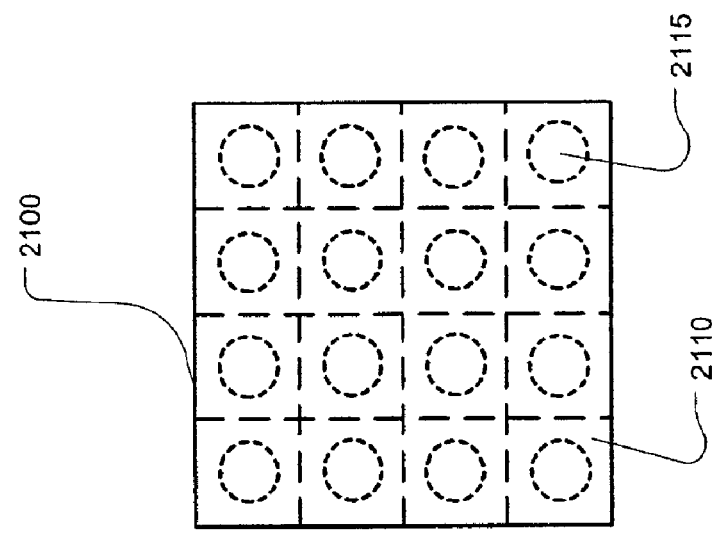

FIGS. 19A–19C show a plan view representing the product packages that correspond to the embodiment of FIG. 18. FIG. 19A shows a blank package 2100 having a four-by-four array of item locations 2110. Each item location includes a tablet well 2115. FIG. 19B shows a filled package 2125. The arrangement of the package 2125 is identical to that of the package 2100 except that tablets 2130 are loaded into each of the tablet wells 2115. Finally, FIG. 19C illustrates how the imaging spectrometer scans the package 2125 one image line at a time. A single row of image pixels 2160 is scanned in a given time frame by the spectrometer. As the package 2125 passes beneath the scanning element, sequential rows of image pixels are scanned until an array of pixels 2155 is formed. The array 2155 represents an image of the package 2125. The package image is then compared to the reference image previously obtained and the item locations can be precisely ascertained.

Figure 20:
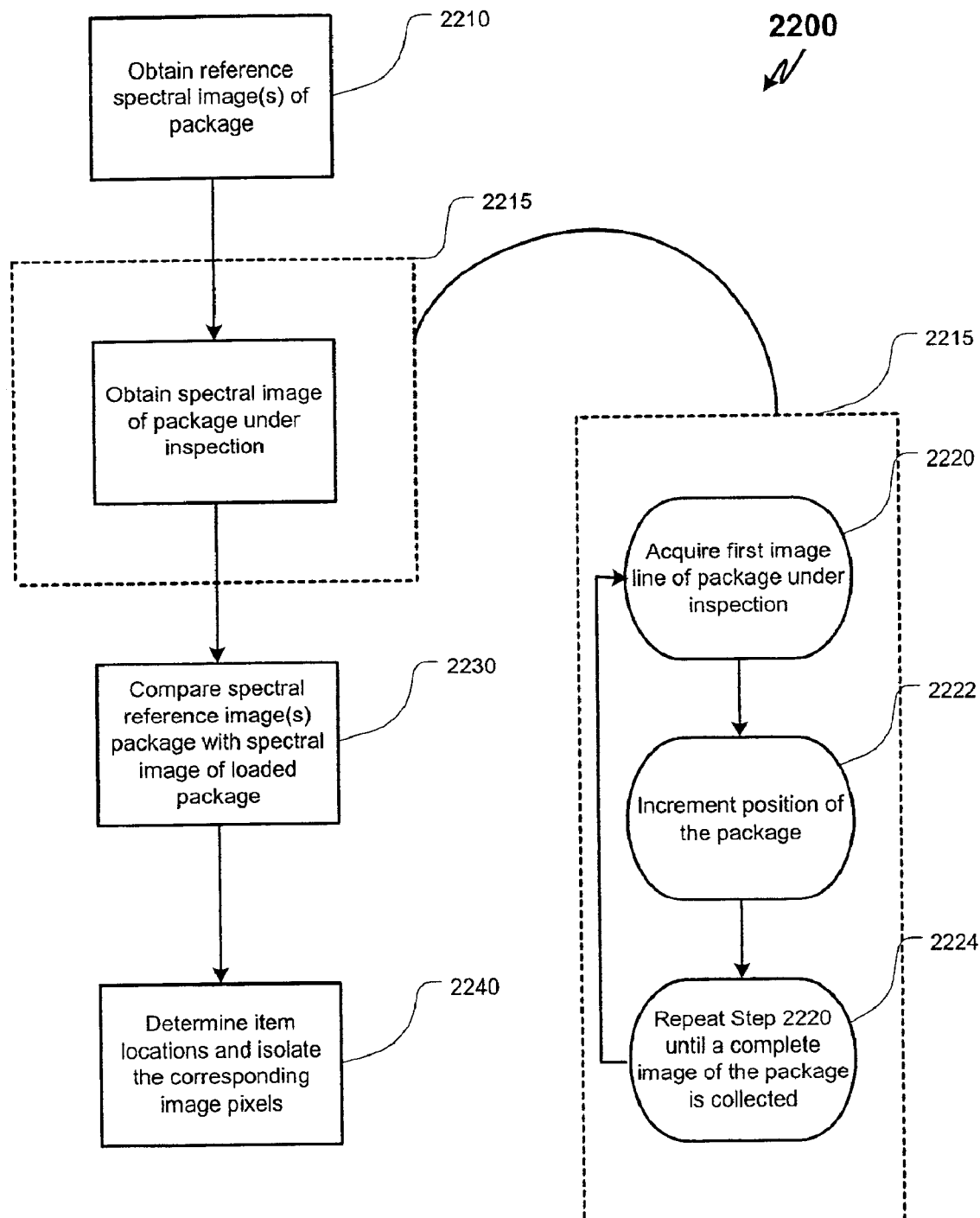
FIG. 20 is a flow chart depicting a method in accordance with an embodiment of the present invention.

FIG. 20 depicts a scanning method 2200 in accordance with an embodiment of the present invention. The spectral reference images of both a blank, unloaded package, and a filled package are first obtained at 2210. The spectral image of a package under inspection is obtained at 2215. Obtaining the spectral image of a package under inspection 2215 is shown in more detail in FIG. 20 as collecting the first line of the image at 2220, incrementing the position of the package at 2222, and looping back to 2220 until the complete image is acquired at 2224. The reference spectral image(s) are compared with the spectral image of the package under inspection at 2230, the item locations are then determined, and the image pixels corresponding to the item locations are isolated at 2240. Spectral analysis of the item compositions can then be accomplished by any of the methods and systems previously described and illustrated as well as by other known inspection systems and methods.

Although the present invention has been described and illustrated in the above description and drawings, it is understood that this description is by example only and that numerous changes and modifications can be made by those skilled in the art without departing from the true spirit and scope of the invention. The invention, therefore, is not to be restricted, except by the following claims and their equivalents.

What is claimed is:

1. A push-broom scanning spectrometer, comprising:
    an imager adapted to simultaneously acquire a line of image pixel from a moving package, wherein the image pixel line comprises a plurality of contiguou spectral bands, wherein the image pixel line is oriented perpendicular to the direction of motion of the package, wherein the package includes a plurality of items;
    a conveyer system adapted to move the package through field of view corresponding to the imager; and a processor capable of being programmed to compare the line of image pixels with a references signal and to determine the location of the plurality of items within the package based on the comparison of the line of image pixels to the reference signal.

2. The push-broom scanning spectrometer of claim 1, wherein the imaging element is a two-dimensional array of photo-detectors.

3. The push-broom scanning spectrometer of claim 1, wherein the line of image pixels corresponds to a plurality of pixel elements.

4. The push-broom scanning spectrometer of claim 1, wherein the scanning spectrometer is incorporated into a pharmaceutical packaging system.

5. The scanning spectrometer of claim 1, wherein the processor is further capable of being programmed to determine the chemical composition of at leas one of the items in the package.

6. The scanning spectrometer of claim 1, wherein the processor is further capable of being programmed to determine the chemical composition of the plurality of items in the package.

7. A push-broom scanning spectrometer, comprising:
    an imager adapted to simultaneously acquire line of image pixels from a moving package, wherein the image pixel line comprises a plurality of contiguous spectral bands, wherein the image pixel line is oriented perpendicular to the direction of motion of the package, wherein the package includes a plurality of items having a chemical composition, and wherein the plurality of contiguous spectral bands corresponds to the chemical composition of the plurality of items;
    a conveyer system adapted to move the through a field of view corresponding to the imager; and
    a processor capable of being programmed to compare the line of image pixels with a references signal and to determine the location of the plurality of items within the package based on the comparison of the line of image pixels to the reference signal.

8. The scanning spectrometer of claim 7, wherein the processor is further capable of being programmed to determine the chemical composition of the plurality of items based on the comparison of the line of image pixels to the reference signal.

9. A method of determining the location of a plurality of items within a package using a scanning spectrometer, comprising:
    acquiring a line of image pixels from a moving package through an imager, wherein the image pixel line comprises a plurality of contiguous spectral bands, wherein the image pixel line is oriented perpendicular to the direction of motion of the package and wherein the package includes a plurality of items having a chemical composition and wherein the plurality of contiguous spectral bands corresponds to the chemical composition of the plurality of items;
    moving the package through a field of view of the imager;
    comparing the line of image pixels with a reference signal; and
    determining the location of the plurality of items within the package based on the comparison of the line of image pixels to the reference signal.

10. The method of claim 9 further comprising determining the chemical composition of at least one of the plurality of items.

11. The method of claim 9 further comprising determining the chemical composition of the plurality of items.

12. The method of claim 9 wherein the package is a blister pack.

13. The method of claim 9 wherein the plurality of items are sealed within the package.

14. The method of claim 9 further comprising storing information corresponding to the location of at least one of the plurality of items.

* * * * *